United States Patent
Alig et al.

[11] Patent Number: 6,001,855
[45] Date of Patent: Dec. 14, 1999

[54] THIAZOLE DERIVATIVES

[75] Inventors: Leo Alig, Kaiseraugst; Albrecht Edenhofer, Riehen; Kurt Hilpert, Hofstetten; Thomas Weller, Basel, all of Switzerland

[73] Assignee: Hoffman-La Roche Inc., Nutley, N.J.

[21] Appl. No.: 09/218,200

[22] Filed: Dec. 22, 1998

[30] Foreign Application Priority Data

Jan. 2, 1998 [EP] European Pat. Off. .............. 98100007

[51] Int. Cl.⁶ ........................ C07D 417/06; A61K 31/425
[52] U.S. Cl. ........................ 514/326; 514/236.8; 514/370; 544/133; 546/270.7; 548/194
[58] Field of Search ........................ 548/194; 546/270.7; 514/326, 370, 236.8; 544/133

[56] References Cited

U.S. PATENT DOCUMENTS 5,763,436  6/1998  Ackermann et al. .

FOREIGN PATENT DOCUMENTS

| 468 231 | 7/1991 | European Pat. Off. . | |
| WO 97/08145 | 3/1997 | WIPO . | |
| WO 97/26250 | 7/1997 | WIPO . | |
| 98/54164 | 12/1998 | WIPO | 514/326 |

OTHER PUBLICATIONS

Barton et al., J.C.S. Perkin I, 162, pp. 159–164 (1982).
Alig et al., J. Med. Chem., 35, pp. 4393–4407 (1992).
Plazzi et al., Il Farmaco, 44, pp. 1011–1030 (1989).
Schnur et al., J. Med. Chem., 34, pp. 914–918 (1991).
Hilpert et al, J. Med. Chem. 37, pp. 3889–3901 (1994).a.

*Primary Examiner*—Robert Gerstl
*Attorney, Agent, or Firm*—George W. Johnston; William H. Epstein; John P. Parise

[57] ABSTRACT

Compounds of formula I

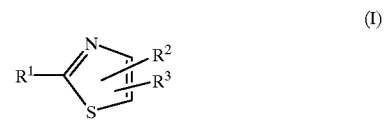

(I)

as well as pharmaceutically usable salts and esters thereof, wherein $R^1$, $R^2$ and $R^3$ have the significance given in claim 1, inhibit the binding of adhesive proteins to the surface of different types of cell and accordingly influence cell-cell and cell-matrix interactions. They can be used in the form of pharmaceutical preparations in the control or prevention of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi.

68 Claims, No Drawings

THIAZOLE DERIVATIVES

BACKGROUND OF THE INVENTION

The present invention is concerned with novel thiazole derivatives that inhibit binding of adhesive proteins to the cell surfaces by influencing cell-cell and cell-matrix interactions.

SUMMARY OF THE INVENTION

The subject invention provides a compound of the formula:

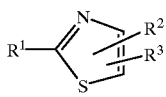

wherein
$R^1$ is

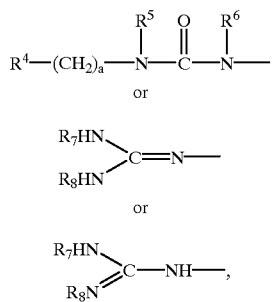

$R^2$ is

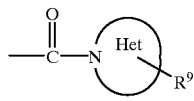

in which Het is a 5- to 8-atom heterocyclic ring that is substituted with $R^9$, the heterocyclic ring contains the depicted nitrogen atom and one atom selected from the group consisting of C, O, N, and S, with the remaining atoms in the heterocyclic ring being C;
$R^3$ is hydrogen, alkyl, cycloalkyl, aryl, aralkyl, or heteroaryl;
$R^4$ is hydrogen, alkyl, cycloalkyl, aryl or, heteroaryl;
$R^5$, $R^6$, $R^7$ and $R^8$ are each independently hydrogen, alkyl, or cycloalkyl, or $R^7$ and $R^8$ together with the N atoms to which they are attached form a 5- to 8-membered heterocyclic ring or 5- to 8-membered heterocyclic ring that is substituted with alkyl;
$R^9$ is

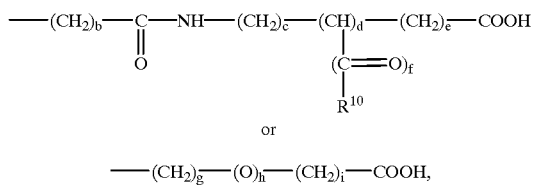

$R^{10}$ is aryl, aralkyl, heterocyclyl, or an α-amino acid bonded via the amino group;

a, b, and c are each independently integers from 0 to 4, d is 0 or 1, e is an integer from 0 to 4, when d is 0 then f is 0, the sum of c, d and e is an integer from 1 to 4, f is 0 or 1, g is an integer from 0 to 5, h is 0 or 1, when h is 1 i is not 0, the sum of g, h and i is an integer from 2 to 5; and pharmaceutically usable salts and esters thereof.

Preferred compounds are where $R^2$ is bonded to position 5 and $R^3$ is bonded to position 4 of the thiazole ring and Het in $R^2$ is a 5- or 6-membered heterocyclic ring. Het preferably contains an O atom in the heterocyclic ring. Favored Hets include pyrrolidine, piperidine, and morpholine. More preferred Hets include a pyrrolidine ring substituted with $R^9$ in the 2- or 3- position, a piperidine ring substituted with $R^9$ in the 3- or 4- position, or a morpholine ring substituted with $R^9$ in the 2- or 3- position.

Favored compounds are where $R^3$ is hydrogen, alkyl, cycloalkyl, phenyl, or phenyl substituted with one or more substituents selected from the group consisting of alkyl, alkoxy, halogen, hydroxy, and amino.

Other favored compounds are where $R^4$ is hydrogen, alkyl, cycloalkyl, phenyl, or phenyl substituted with one or more substituents selected from the group consisting of alkyl, alkoxy, halogen, hydroxy, and amino. $R^5$, $R^6$, $R^7$ and $R^8$ are preferably hydrogen or $R^5$ and $R^6$ are each hydrogen and $R^7$ and $R^8$ together with the N atoms to which they are attached form a 5- or 6-membered heterocyclic ring. More preferred are where $R^5$, $R^6$, $R^7$ and $R^8$ are all hydrogen.

$R^{10}$ is favorably phenyl, pyridyl, phenyl substituted with one or more substituents selected from the group consisting of alkyl, alkoxy, halogen, hydroxy and amino, or pyridyl substituted with one or more substituents selected from the group consisting of alkyl, alkoxy, halogen, hydroxy and amino. An especially preferred embodiment is where $R^{10}$ is phenyl and f is 0.

A subgenus of preferred compounds have the formula:

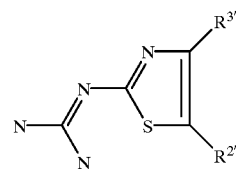

Ia wherein
$R^{2'}$ is

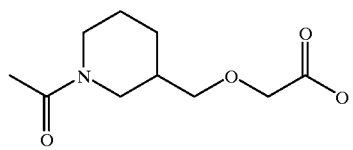

and
$R^{3'}$ is alkyl, cycloalkyl, or phenyl.

The subject compounds can be used in a pharmaceutical composition that includes the compound, a pharmaceutically acceptable carrier, and perhaps other ingredients. The compounds, preferably as a pharmaceutical composition, can be used for treating or preventing illnesses caused by a malfunction of the binding of adhesive proteins to vitronectin receptors. This method of treatment or prevention comprises administering to a subject in need of such treating or preventing an effective amount of a subject compound.

The subject invention also provides a process for manufacturing the above compounds. This process involves reacting a thiazolecarboxylic acid of formula:

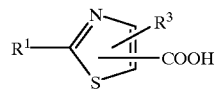
(II)

with an amine of formula:

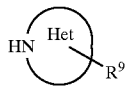
(III)

or a salt thereof, wherein $R^1$, $R^3$, $R^9$ and Het are as above.

The subject invention also provides novel intermediates having the formula:

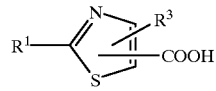
(II)

wherein
$R^1$ is

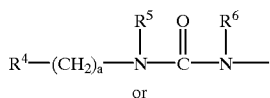

or

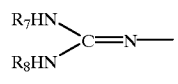

or

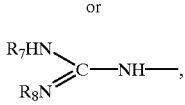

$R^3$ is hydrogen, alkyl, cycloalkyl, aryl, aralkyl, or heteroaryl;
$R^4$ is hydrogen, alkyl, cycloalkyl, aryl or, heteroaryl;
$R^5$, $R^6$, $R^7$ and $R^8$ are each independently hydrogen, alkyl, or cycloalkyl, or $R^7$ and $R^8$ together with the N atoms to which they are attached form a 5- to 8-membered heterocyclic ring or 5- to 8-membered heterocyclic ring that is substituted with alkyl;
and pharmaceutically usable salts and esters thereof;
with the proviso that, in the case of the acids, when $R^1$ is

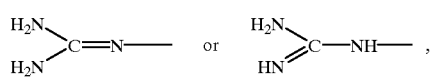

$R^3$ is not hydrogen or methyl, and, in the case of the esters, $R^3$ is not hydrogen, methyl or pyrid-4-yl N-oxide.

Preferred intermediates are compounds having the formula:

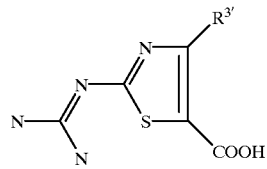
IIa wherein
$R^{3'}$ is alkyl, cycloalkyl, or phenyl.

Preferred $R^3$ include where alkyl is methyl, propyl or t-butyl, and cycloalkyl is cyclopentyl.

DETAILED DESCRIPTION OF THE PREFERRED EMBODIMENTS

The present invention will now be described in terms of its preferred embodiments. These embodiments are set forth to aid in understanding the invention but are not to be construed as limiting.

The present invention is concerned especially with thiazole derivatives of formula I

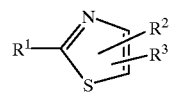
(I)

wherein
$R^1$ is

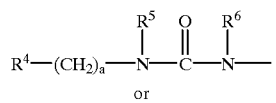

or

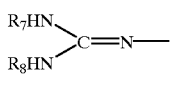

or

$R^2$ is

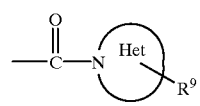

in which Het is a 5- to 8-membered heterocyclic ring system, which is substituted with $R^9$ and in which an additional N,O or S atom can be present in the ring in addition to the nitrogen atom,
$R^3$ is hydrogen, alkyl, cycloalkyl, aryl, aralkyl or heteroaryl;
$R^4$ is hydrogen, alkyl, cycloalkyl, aryl or heteroaryl;
$R^5$, $R^6$, $R^7$ and $R^8$ are each independently hydrogen, alkyl or cycloalkyl or $R^7$ and $R^8$ together with the N atoms to which they are attached form a 5- to 8-membered heterocyclic ring which can be substituted with alkyl;

$R^9$ is

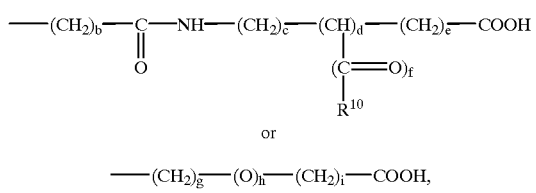

or

—$(CH_2)_g$—$(O)_h$—$(CH_2)_i$—COOH, $R^{10}$ is aryl, aralkyl, heterocyclyl or an α-amino acid bonded via the amino group, a to i are zero or whole positive numbers, whereby a and b are each independently zero to 4, d is zero or 1, with f being equal to zero when d is equal to zero, the sum of c, d and e is ≧1 and ≦4, f and h are each independently zero or 1, with i being other than zero when h=1, the sum of g, h and i is ≧2 and ≦5; and their pharmaceutically usable salts and esters.

The compounds of formula I and their pharmaceutically usable salts and esters are novel and have valuable pharmacological properties. In particular, they inhibit the binding of adhesive proteins such as fibrinogen, vitronectin, von Willebrand factor, fibronectin, thrombospondin and osteopontin to the vitronectin receptors (such as e.g. $α_vβ_3$, $α_vβ_5$, $α_vβ_6$, $α_vβ_8$, etc.) on the surface on different types of cell. The compounds therefore influence cell-cell and cell-matrix interactions. They can be used as vitronectin receptor antagonists in the prophylaxis or treatment of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi.

Objects of the present invention are the compounds of formula I and their aforementioned salts and esters, and their use as therapeutically active substances, a process for the manufacture of the said compounds, intermediates, pharmaceutical compositions, medicaments which contain the compounds, their salts or esters, the use of the compounds, solvates and salts as medicaments, especially for the prophylaxis and/or therapy of illnesses (e.g. in the treatment or prophylaxis of neoplasms, tumor metastasing, osteoporosis, Paget's disease, diabetic retinopathy, macular degeneration, restenosis following vascular intervention, psoriasis, arthritis, kidney failure, as well as infections caused by viruses, bacteria or fungi), and the use of the compounds and salts and/or esters for the production of medicaments for the treatment or prophylaxis of, for example, neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi.

In the present description the term "alkyl", alone or in combination, signifies a straight-chain or branched-chain alkyl group with 1 to 8 carbon atoms, preferably a straight-chain or branched-chain alkyl group with 1–4 carbon atoms. Examples of straight-chain and branched-chain $C_1$–$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, isopropyl and tert-butyl.

The term "cycloalkyl", alone or in combination, signifies a cycloalkyl ring with 3 to 8 carbon atoms, preferably a cycloalkyl ring with 5 to 7 carbon atoms. Examples of $C_3$–$C_8$ cycloalkyl rings are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopentyl.

The term "alkoxy", alone or in combination, signifies an alkyl ether group in which the term "alkyl" has the previously given significance. Examples are methoxy, ethoxy, n-propoxy, isopropoxy, n-butoxy, isobutoxy, sec.butoxy and tert.butoxy, with methoxy and ethoxy being preferred.

The term "aryl", alone or in combination, signifies a phenyl or naphthyl group which optionally carries one or more substituents each independently selected from alkyl, alkoxy, halogen, hydroxy, amino and the like, such as phenyl, p-tolyl, 4-methoxyphenyl, 4-tert.butoxyphenyl, 4-fluorophenyl, 2-chlorophenyl, 3-chlorophenyl, 4-chlorophenyl, 4-hydroxyphenyl, 1-naphthyl and 2-naphthyl. Phenyls and chlorophenyls are preferred, especially phenyl and ortho-, meta- and para-monochlorophenyls.

The term "aralkyl", alone or in combination, signifies an alkyl or cycloalkyl group as previously defined in which one hydrogen atom is replaced by an aryl group as previously defined, such as benzyl, 2-phenylethyl and the like, with benzyl being preferred.

The term "Het" denotes the hydrocyclic system

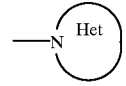

in $R^2$, i.e. a saturated, partially unsaturated or aromatic 5- to 8-membered heterocycle which carries $R^9$ as a substituent and which can contain in addition to the nitrogen atom an additional nitrogen, oxygen or sulfur atom, with the oxygen atom being preferred of these. If desired, it can be substituted on one or more carbon atoms by halogen, alkyl, cycloalkyl, alkoxy, oxo etc. and/or on a secondary nitrogen atom (i.e. —NH—) by alkyl, cycloalkyl, aralkoxycarbonyl, alkanoyl, phenyl or phenylalkyl. Examples of such heterocyclic ring systems are the pyrrolidine, piperidine, piperazine, morpholine, thiamorpholine, pyrrole, imidazole, pyrazole or hexahydropyrimidine ring. Preferred are 5- or 6-membered rings and of these especially the pyrrolidine, piperidine and morpholine rings.

The term "heterocyclyl", alone or in combination, signifies a saturated, partially unsaturated or aromatic 5- to 10-membered heterocycle which contains one or more hetero atoms selected from nitrogen, oxygen and sulphur. If desired, it can be substituted on one or more carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl. Examples of such heterocyclyl groups are pyrrolidinyl, piperidinyl, piperazinyl, morpholinyl, thiamorpholinyl, pyrrolyl, imidazolyl (e.g. imidazol-4-yl and 1-benzyloxy-carbonylimidazol-4-yl), pyrazolyl, pyridyl, pyrazinyl, pyrimidinyl, hexahydropyrimidinyl, furyl, thienyl, thiazolyl, oxazolyl, thiazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2, 3,4-tetrahydro-2-quinolyl), 1,2, 3,4-tetrahydroisoquinolyl (e.g. 1,2,3,4-tetrahydro-1-oxo-isoquinolyl) and quinoxalinyl. Preferred are 5- or 6-membered rings and of these especially piperidyl and pyridyl.

The term "heteroaryl", alone or in combination, signifies the aromatic compounds which fall under the definition of "heterocyclyl", with 5- and 6-membered rings, especially pyridyl, being preferred.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two substituents on the nitrogen together forming a ring, such as, for example, $NH_2$, methylamino, ethylamino, dimethylamino, diethylamino, methylethylamino, pyrrolidin-yl or piperidino etc. Primary amino, dimethylamino and diethylamino are preferred.

The term "halogen" signifies fluorine, chlorine, bromine or iodine, preferably chlorine.

Examples of "α-amino acids" bonded via the amino group are α-amino acids having the L- or D-configuration, the carboxyl group of which can be optionally derivatised as an ester or amide. Examples of such α-amino acids are L-valine, L-phenylalanine, L-leucine, L-isoleucine, L-serine, L-threonine, 3-(1-naphthyl)-L-alanine, 3-(2-naphthyl)-L-alanine, N-isopropyl-glycine, β-cyclohexyl-L-alanine and L-proline. Preferred are alanine, valine, phenylalanine, leucine and β-cyclohexyl-alanine, especially valine.

In the nomenclature used in the present description the ring atoms of the thiazole ring are numbered as follows:

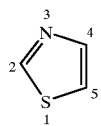

with substituent $R^1$ being bonded to position 2 and substituent $R^2$ being bonded to position 4 and substituent $R^3$ being bonded to position 5:

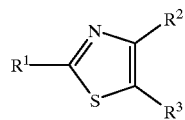

or substituent $R^2$ being bonded to position 5 and substituent $R^3$ being bonded to position 4 of the thiazole ring:

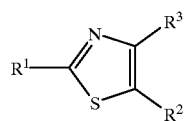

In the most preferred arrangement $R^2$ is situated in position 5 and $R^3$ is situated in position 4 of the thiazole ring.

Examples of physiologically usable salts of the compounds of formula I are salts with physiologically compatible mineral acids such as hydrochloric acid, sulphuric acid or phosphoric acid; or with organic acids such as methanesulphonic acid, acetic acid, trifluoroacetic acid, citric acid, fumaric acid, maleic acid, tartaric acid, succinic acid or salicylic acid. The compounds of formula I having a free carboxy group can also form salts with physiologically compatible bases. Examples of such salts are alkali metal, alkaline earth metal, ammonium and alkylammonium salts such as the Na, K, Ca or tetramethylammonium salt. The compounds of formula I can also exist in the form of zwitterions.

The invention expressly includes pharmaceutically suitable derivatives of the compounds of formula I. For example, the COOH groups in $R^2$ can be esterified. Examples of suitable esters are the alkyl and aralkyl esters. Preferred esters are the methyl, ethyl, propyl, butyl, benzyl and (R/S)-1-((isopropoxy-carbonyl)-oxy)-ethyl esters. The ethyl esters are especially preferred.

The compounds of formula I can also be solvated, e.g. hydrated. The hydration can be effected in the course of the manufacturing process or can take place as a consequence of hygroscopic properties of an initially anhydrous compound of formula I.

The compounds of formula I can contain several asymmetric centers and can exist in the form of optically pure enantiomers, mixtures of enantiomers, racemates, optically pure diastereoisomers, mixtures of diastereoisomers, diastereoisomeric racemates or mixtures of diastereoisomeric racemates.

Preferred compounds of formula I are those in which substituent $R^2$ is bonded to position 5 and substituent $R^3$ is bonded to position 4 of the thiazole ring.

Also preferred are compounds of formula I in which Het in $R^2$ is a 5- or 6-membered heterocyclic ring system. Likewise preferred are those compounds of formula I in which Het is a 5- or 6-membered heterocyclic ring system in which an oxygen atom is present in the ring.

A group of especially preferred compounds of formula I comprises those in which Het in $R^2$ is a pyrrolidine, piperidine or morpholine ring and especially in which Het in $R^2$ is a pyrrolidine ring substituted with $R^9$ in the 2- or 3-position, a piperidine ring substituted with $R^9$ in the 3- or 4-position or a morpholine ring substituted with $R^9$ in the 2- or 3-position.

Furthermore, preferred compounds are those in which $R^3$ is hydrogen, alkyl, cycloalkyl, phenyl or substituted phenyl in which the substituted phenyl carries one or more substituents selected from alkyl, alkoxy, halogen, hydroxy, nitro and amino.

Likewise preferred compounds are those in which $R^4$ is hydrogen, alkyl, cycloalkyl, phenyl or substituted phenyl in which the substituted phenyl carries one or more substiutents selected from alkyl, alkoxy, halogen, hydroxy and amino.

A further group of preferred compounds comprises those in which $R^5$, $R^6$, $R^7$ and $R^8$ are hydrogen or $R^5$ and $R^6$ are hydrogen and $R^7$ and $R^8$ together with the N atoms to which they are attached form a 5- or 6-membered heterocyclic ring which can be substituted by alkyl, especially an imidazolidine or hexahydropyrimidine ring. Compounds in which $R^5$, $R^6$, $R^7$ and $R^8$ are hydrogen are especially preferred.

Furthermore, there are preferred compounds in which $R^{10}$ is phenyl, pyridyl, substituted pyridyl or substituted phenyl, with the substituted phenyl and the substituted pyridyl carrying one or more substituents selected from alkyl, alkoxy, halogen, hydroxy and amino. Compounds in which $R^{10}$ is phenyl are especially preferred. Compounds in which $R^{10}$ is phenyl and f is equal to 0 are particularly preferred.

A group of preferred compounds of formula I comprises those in which substituent $R^2$ is bonded to position 5 and substituent $R^3$ is bonded to position 4 of the thiazole ring, Het in $R^2$ is a 5- or 6-membered heterocyclic ring system in which $R^9$ is bonded to one of the ring carbon atoms and in which optionally additionally an oxygen atom can be present in the ring, $R^3$ is hydrogen, alkyl, cycloalkyl, phenyl or substituted phenyl, with the substituted phenyl carrying one or more substitutents selected from alkyl, cycloalkyl, alkoxy, halogen, hydroxy, nitro and amino, $R^4$ is hydrogen, alkyl, cycloalkyl, phenyl or substituted phenyl, with the substituted phenyl carrying one or more substituents selected from alkyl, alkoxy, halogen, hydroxy and amino, $R^5$, $R^6$, $R^7$ and $R^8$ are hydrogen or $R^7$ and $R^8$ together with the N atoms to which they are attached form a 5- or 6-membered heterocyclic ring which can be substituted by alkyl, $R^{10}$ is phenyl, pyridyl, substituted pyridyl or substituted phenyl, with the substituted phenyl and the substituted pyridyl carrying one or more substituents selected from alkyl, alkoxy, halogen, hydroxy and amino, a and b each independently are zero to 3, the sum of c, d and e is $\geq 1$ and $\leq 3$ and the sum of g, h and i is $\geq 2$ and $\leq 4$.

A group of especially preferred compounds of formula I comprises those in which substituent $R^2$ is bonded to position 5 and substituent $R^3$ is bonded to position 4 of the thiazole ring, Het in $R^2$ is a pyrrolidine ring substituted with $R^9$ in the 2- or 3-position, a piperidine ring substituted with $R^9$ in the 3- or 4-position or a morpholine ring substituted with $R^9$ in the 2- or 3-position, $R^3$ is hydrogen, alkyl or phenyl, $R^4$ is hydrogen, alkyl or phenyl, $R^5$, $R^6$, $R^7$ and $R^8$ are hydrogen or $R^7$ and $R^8$ together with the N atoms to which they are attached form an imidazolidine of hexahydropyrimidine ring and especially preferably $R^5$, $R^6$, $R^7$ and $R^8$ are hydrogen, $R^{10}$ is phenyl and especially preferably $R^{10}$ is phenyl and simultaneously f is equal to 0, a and b are each independently zero to 2 and the sum of g, h and i is equal to 2 or 3.

Examples of preferred compounds of formula I are:

Ethyl (RS)-3-[[1-(2-guanidino-4-methyl-thiazole-5-carbonyl)-piperidine-3-carbonyl]-amino]-propionate;

(RS)-3-[[1-(2-guanidino-4-methyl-thiazole-5-carbonyl)-piperidine-3-carbonyl]-amino]-propionic acid hydrochloride;

[1-(2-guanidino-4-methyl-thiazole-5-carbonyl)-piperidin-4-yloxy]-acetic acid trifluoroacetate;

ethyl (RS)-3-[[1-(2-guanidino-thiazole-4-carbonyl)-piperidine-3-carbonyl]-amino]-propionate;

(RS)-3-[[1-(2-guanidino-thiazole-4-carbonyl)-piperidine-3-carbonyl]-amino]-propionic acid;

(R)-[1-(2-guanidino-4-methyl-thiazole-5-carbonyl)-pyrrolidin-3-ylmethoxy]-acetic acid;

(S)-[1-(2-guanidino-4- methyl-thiazole-5-carbonyl)-pyrrolidin-3-ylmethoxy]-acetic acid;

ethyl (RS)-[1-(2-guanidino-thiazole-5-carbonyl)-piperidin-3-ylmethoxy]-acetate;

(RS)-[1-(2-guanidino-thiazole-5-carbonyl)-piperidin-3-ylmethoxy]-acetic acid hydrochloride;

ethyl (RS)- and (SR)-3-[[(RS)-1-(2-guanidino-4-methyl-thiazole-5-carbonyl)-piperidine-3-carbonyl]-amino]-3-phenyl-propionate;

(RS)- and (SR)-3-[[(RS)-1-(2-guanidino-4-methyl-thiazole-5-carbonyl)-piperidine-3-carbonyl]-amino]-3-phenyl-propionic acid;

ethyl rac [1-(2-guanidino-thiazole-4-carbonyl)-piperidin-3-ylmethoxy]-acetate;

ethyl rac [1-(2-guanidino-4-methyl-thiazole-5-carbonyl)-piperidin-3-ylmethoxy]-acetate hexafluorophosphate;

ethyl rac [1-(2-guanidino-4-propyl-thiazole-5-carbonyl)-piperidin-3-ylmethoxy]-acetate;

ethyl rac [1-(2-guanidino-4-phenyl-thiazole-5-carbonyl)-piperidin-3-ylmethoxy]-acetate;

ethyl rac [1-(4-tert-butyl-2-guanidino-thiazole-5-carbonyl)-piperidin-3-ylmethoxy]-acetate;

ethyl rac [1-(4-cyclopentyl-2-guanidino-thiazole-5-carbonyl)-piperidin-3-ylmethoxy]-acetate;

rac [1-(2-guanidino-thiazole-4-carbonyl)-piperidin-3-ylmethoxy]-acetic acid;

rac [1-(2-guanidino-4-methyl-thiazole-5-carbonyl)-piperidin-3-ylmethoxy]-acetic acid;

rac [1-(2-guanidino-4-propyl-thiazole-5-carbonyl)-piperidin-3-ylmethoxy]-acetic acid;

rac [1-(2-guanidino-4-phenyl-thiazole-5-carbonyl)-piperidin-3-ylmethoxy]-acetic acid;

rac [1-(4-tert-butyl-2-guanidino-thiazole-5-carbonyl)-piperidin-3-ylmethoxy]-acetic acid;

rac [1-(4-cyclopentyl-2-guanidino-thiazole-5-carbonyl)-piperidin-3-ylmethoxy]-acetic acid;

ethyl (S)-[1-(2-guanidino-4-methyl-thiazole-5-carbonyl)-piperidin-3-ylmethoxy]-acetate;

ethyl (R)-[1-(2-guanidino-4-methyl-thiazole-5-carbonyl)-piperidin-3-ylmethoxy]-acetate;

ethyl rac [1-(2-guanidino-4-methyl-thiazole-5-carbonyl)-pyrrolidin-2-ylmethoxy]-acetate;

ethyl rac 3-[1-(2-guanidino-4-methyl-thiazole-5-carbonyl)-piperidin-3-ylmethoxy]-propionate;

ethyl rac [4-(2-guanidino-4-methyl-thiazole-5-carbonyl)-morpholin-2-ylmethoxy]-acetate;

ethyl [1-(2-guanidino-4-methyl-thiazole-5-carbonyl)-piperidin-4-ylmethoxy]-acetate;

(S)-[1-(2-guanidino-4-methyl-thiazole-5-carbonyl)-piperidin-3-ylmethoxy]-acetic acid;

(R)-[1-(2-guanidino-4-methyl-thiazole-5-carbonyl)-piperidin-3-ylmethoxy]-acetic acid;

rac [1-(2-guanidino-4-methyl-thiazole-5-carbonyl)-pyrrolidin-2-ylmethoxy]-acetic acid;

rac 3-[1-(2-guanidino-4-methyl-thiazole-5-carbonyl)-piperidin-3-ylmethoxy]-propionic acid;

rac [4-(2-guanidino-4-methyl-thiazole-5-carbonyl)-morpholin-2-ylmethoxy]-acetic acid;

[1-(2-guanidino-4-methyl-thiazole-5-carbonyl)-piperidin-4-ylmethoxy]-acetic acid;

ethyl rac [1-[2-(3-benzyl-ureido)-4-methyl-thiazole-5-carbonyl]-piperidin-3-ylmethoxy]-acetate;

rac [1-[2-(3-benzyl-ureido)-4-methyl-thiazole-5-carbonyl]-piperidin-3-ylmethoxy]-acetic acid;

ethyl [1-(2-guanidino-thiazole-4-carbonyl)-piperidin-4-ylmethoxy-acetate;

ethyl rac [1-(2-guanidino-4-methyl-thiazole-5-carbonyl)-piperidin-3-yloxy]-acetate;

ethyl rac [1-[4-methyl-2-(3-methyl-ureido)-thiazole-5-carbonyl]-piperidin-3-ylmethoxy]-acetate;

[1-(2-guanidino-thiazole-4-carbonyl)-piperidin-4-ylmethoxy]-acetic acid;

rac [1-(2-guanidino-4-methyl-thiazole-5-carbonyl)-piperidin-3-yloxy]-acetic acid; and rac [1-[4-methyl-2-(3-methyl-ureido)-thiazole-5-carbonyl]-piperidin-3-ylmethoxy]-acetic acid.

Examples of especially preferred compounds of formula I are the following:

rac [1-(2-guanidino-4-propyl-thiazole-5-carbonyl)-piperidin-3-ylmethoxy]-acetic acid;

rac [1-(2-guanidino-4-methyl-thiazole-5-carbonyl)-piperidin-3-ylmethoxy]-acetic acid;

(R)-[1-(2-guanidino-4-methyl-thiazole-5-carbonyl)-piperidin-3-ylmethoxy]-acetic acid;

rac [1-(2-guanidino-4-phenyl-thiazole-5-carbonyl)-piperidin-3-ylmethoxy]-acetic acid;

rac [1-(4-cyclopentyl-2-guanidino-thiazole-5-carbonyl)-piperidin-3-ylmethoxy]-acetic acid; and rac [1-(4-tert-butyl-2-guanidino-thiazole-5-carbonyl)-piperidin-3-ylmethoxy]-acetic acid.

Also an object of the invention is a process for the manufacture of a compound of formula I in which a thiazolecarboxylic acid of formula II

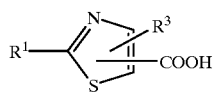 (II)

is reacted with an amine of formula III

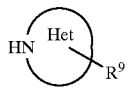 (III)

or a salt thereof, with $R^1$, $R^3$, $R^9$ and Het having the previously given significance.

Especially preferred is a process in which the coupling of the thiazolecarboxylic acid with the amine component is effected by means of a coupling reagent and under the influence of a base. Especially suitable coupling reagents are, for example, benzotriazol-1-yloxy-tris(dimethylamino) phosphonium hexafluorophosphate (BOP) or O-(benzotriazol-1-yl)-N, N, N',N'-tetramethyluronium hexafluorophosphate (HBTU). Suitable bases are e.g. 4-methylmorpholine or N-methylmorpholine. All solvents which are inert under the given conditions can be used as the solvent. DMF is a preferred solvent for the reaction.

A further object of the invention comprises the intermediates of formula II

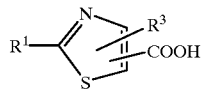 (II)

wherein $R^1$ and $R^3$ have the significances given above, with the proviso that, in the case of the acids, $R^3$ is not hydrogen or methyl when $R^1$ is

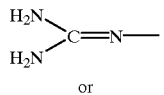

or

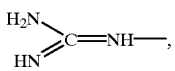

and, in the case of the esters, $R^3$ is not hydrogen, methyl or pyrid-4-yl N-oxide.

Particularly preferred intermediates are:
Ethyl 2-guanidino-4-propyl-thiazole-5-carboxylate hydrobromide;
ethyl 2-guanidino-4-phenyl-thiazole-5-carboxylate hydrobromide;
ethyl 4-tert-butyl-2-guanidino-thiazole-5-carboxylate hydrobromide;
ethyl 4-cyclopentyl-2-guanidino-thiazole-5-carboxylate hydrobromide;
2-guanidino-4-methyl-thiazole-5-carboxylic acid;
2-guanidino-4-propyl-thiazole-5-carboxylic acid hydrochloride;
2-guanidino-4-phenyl-thiazole-5-carboxylic acid;
4-tert-butyl-2-guanidino-thiazole-5-carboxylic acid hydrochloride;
4-cyclopentyl-2-guanidino-thiazole-5-carboxylic acid hydrochloride;
ethyl 2-(3-benzyl-ureido)-4-methyl-thiazole-5-carboxylate;
2-(3-benzyl-ureido)-4-methyl-thiazole-5-carboxylic acid;
tert-butyl rac 3-carboxymethoxymethyl-piperidine-1-carboxylate;
tert-butyl (S)-3-carboxymethoxymethyl-piperidine-1-carboxylate;
tert-butyl (R)-3-carboxymethoxymethyl-piperidine-1-carboxylate;
tert-butyl rac 2-carboxymethoxymethyl-pyrrolidine-1-carboxylate;
ethyl rac (4-benzyl-morpholin-2-ylmethoxy)-acetate;
ethyl rac (morpholin-2-ylmethoxy)-acetate hydrochloride;
tert-butyl 4-ethoxycarbonylmethoxymethyl-piperidine-1-carboxylate;
ethyl (piperidin4-ylmethoxy)-acetate;
tert-butyl rac 3-carboxymethoxy-piperidine-1-carboxylate;
ethyl rac (piperidin-3-yloxy)-acetate hydrochloride;
4-methyl-2-(3-methyl-ureido)-thiazole-5-carboxylic acid;
tert-butyl (RS)- 3-(2-ethoxycarbonyl-ethylcarbamoyl)-piperidine-1-carboxylate;
ethyl (RS)-3-[(piperidine-3-carbonyl)-amino]-propionate hydrochloride;
tert-butyl (R)-[1-(R)-[1-phenyl-ethyl]-pyrrolidin-3-ylmethoxy]-acetate;
tert-butyl (R)-(pyrrolidin-3-ylmethoxy)-acetate;
tert-butyl (R)-[1-(2-guanidino-4-methyl-thiazole-5-carbonyl)-pyrrolidin-3-ylmethoxy]-acetate;
tert-butyl (S)-[1-(R)-[1-phenyl-ethyl]-pyrrolidin-3-ylmethoxy]-acetate;
tert-butyl (S)-(pyrrolidin-3-ylmethoxy)-acetate;
tert-butyl (S)-[1-(2-guanidino-4-methyl-thiazole-5-carbonyl)-pyrrolidin-3-ylmethoxy]-acetate;
tert-butyl 3-(2-ethoxycarbonyl-1-phenyl-ethylcarbamoyl)-piperidine-1-carboxylate;
ethyl (RS)-3-phenyl-3-[(RS)-(piperidine-3-carbonyl)-amino]-propionate hydrochloride; and
tert-butyl [1-(2-guanidino-4-methyl-thiazole-5-carbonyl)-piperidin-4-yloxy]-acetate;

Compounds of formula I described above for use as therapeutically active substances are a further object of the invention.

Also an object of the invention are compounds of formula I described above for the production of medicaments for the prophylaxis and therapy of illnesses which are caused by a malfunction of the binding of adhesive proteins to vitronectin receptors.

Likewise an object of the invention are medicaments or pharmaceutical compositions containing a compound of formula I described above and a therapeutically inert carrier.

Also objects of the invention are the above medicaments which additionally contain one or more compounds selected from the group consisting of compounds of formula I, blood platelet inhibitors, anticoagulants, fibrinolytics as well as medicaments for the prophylaxis and therapy of illnesses which are caused by a malfunction of the binding of adhesive proteins to vitronectin receptors.

An object of the invention is also the use of the compounds of formula I described above for the production of medicaments e.g. for the treatment for prophylaxis of illnesses which are caused by a malfunction of the binding of adhesive proteins to vitronectin receptors.

Also an object of the invention is the use of one of the compounds of formula I described above for the production of medicaments for the treatment or prophylaxis of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi.

A further object of the invention comprises compounds of formula I when manufactured according to one of the described processes.

Likewise objects of the invention are methods for the treatment and prophylaxis of illnesses which are caused by a malfunction of the binding of adhesive proteins to vitronectin receptors and which comprise the administration of an effective amount of a compound of formula I.

An object of the invention is, further, a method for the treatment and prophylaxis of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi, whereby an effective amount of a compound of formula I described above is administered.

Also an object of the invention are compounds of formula I described above for the treatment and prophylaxis of neoplasms, tumor metastasing, osteoporosis, Paget's disease, diabetic retinopathy, macular degeneration, restenosis following vascular intervention, psoriasis, arthritis, kidney failure and infections caused by viruses, bacteria or fungi.

The compounds of formula I hereinbefore and their pharmaceutically usable salts and esters are manufactured by the processes which are made available by the present invention. The substituents used in the following Schemes have the significance given above.

The compounds in accordance with the invention are manufactured by reacting a thiazolecarboxylic acid of the formula

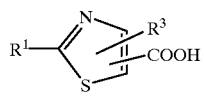

(II)

with an amine of the formula

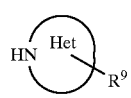

(III)

or a salt thereof with intermediary protection of the carboxy groups present in $R^9$.

The coupling of the thiazolecarboxylic acid with the amine component is effected by means of a coupling reagent such as benzotriazol-1-yloxy-tris(dimethylamino)-phosphonium hexafluorophosphate (BOP) or O-(benzotriazol-1-yl)-N,N,N',N'-tetramethyluronium hexafluorophosphate (HBTU) under the influence of a base such as 4-ethylmorpholine or N-methylmorpholine (N-MM) in an inert solvent such as DMF at room temperature (Scheme 1).

Scheme 1

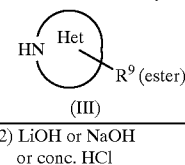
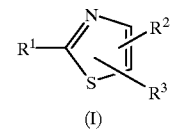
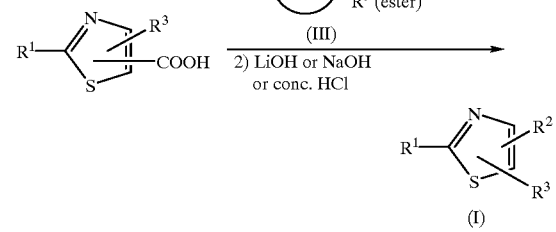

(I)

The subsequent liberation of the carboxy group protected as an ester is effected by means of a base such as aqueous LIOH or aqueous NaOH or also by cleavage using a strong acid such as concentrated hydrochloric acid or, in the case of a tert.butyl ester, trifluoroacetic acid.

For the preparation of the aforementioned thiazolecarboxylic acids [*J. Med. Chem.*, 34: 914 (1991)], conveniently an α-bromo-ketone of formula IV, such as e.g. a pyruvic acid ester, is reacted in a solvent such as ethanol with a thiourea derivative of formula V, such as 2-imino-4-thiobiuret, at elevated temperature (Scheme 2a).

Scheme 2a

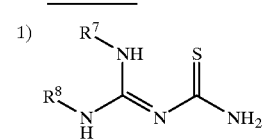
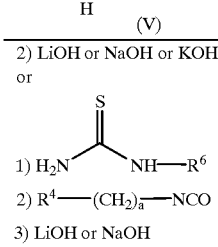
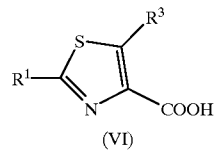

(VI)

A subsequent saponification of the ester group such as ethoxycarbonyl using a base such as aqueous NaOH or KOH yields a thiazole-4-carboxylic acid derivative of formula VI.

In another process variant, a substituted thiourea after cyclization to the thiazole can be reacted with an isocyanate such as benzyl isocyanate in a solvent such as DMF at room temperature, followed by a saponification of the ester as described above.

In a further process variant (Scheme 2b), which analogously to the process described above yields thiazole-5-carboxylic acid derivatives of formula II [*Famaco*, 44: 1011 (1989)], there are used α-haloketones of formula VIII.

Scheme 2b

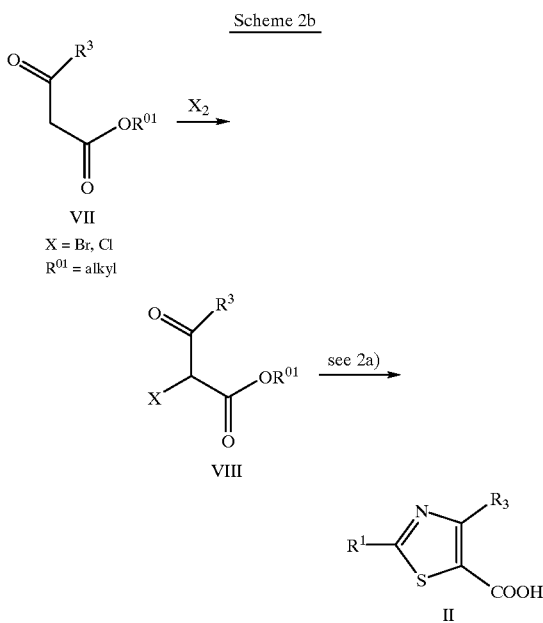

The α-haloketones of formula VIII are prepared from the corresponding α-ketoesters, such as ethyl butyrylacetate, ethyl pivaloylacetate, etc., by halogenation with e.g. bromine in a solvent such as water, conveniently at a temperature of 0–5° C. (J. Chem. Soc. Perkin I 1982, 162).

For the preparation of the aforementioned amine components, an aminoalcohol protected with $R^{02}$ in which $R^{02}$ is a nitrogen protecting group such as Boc, benzyl or α-methylbenzyl is conveniently reacted with a bromoalkanoic acid ester, such as ethyl bromoacetate or ethyl bromopropionate, in the presence of a strong base such as aqueous NaOH (Scheme 3a).

Scheme 3a

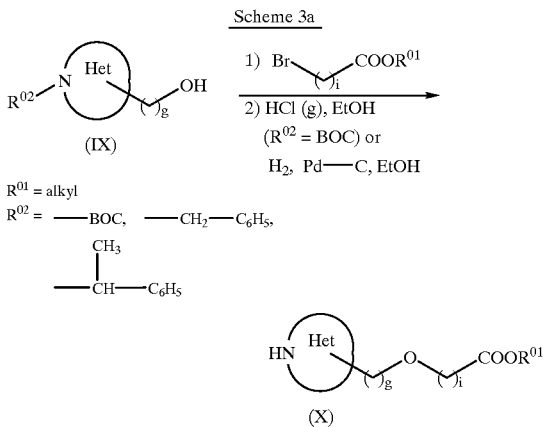

A saponification of the ester function which may have taken place is counteracted either prior to the cleavage or simultaneously with the cleavage of the nitrogen protecting group by esterification of the liberated carboxylic acid. The nitrogen protecting group Boc is cleaved off using hydrochloric acid in an alcohol equivalent to the ester, such as methanol or ethanol. The cleavage of the benzyl or α-methylbenzyl protecting group is accomplished by hydrogenation in ethanol in the presence of Pd/C. When a second nitrogen atom is present in the heterocycle, then both nitrogen atoms must each be bonded to different protecting groups.

In a process variant, the amine component can also be prepared from an aromatic precursor, such as e.g. pyridinylmethoxy-acetic acid, by hydrogenation in a solvent such as acetic acid and in the presence of Pt/C, preferably at elevated temperature and elevated pressure (Scheme 3b).

Scheme 3b

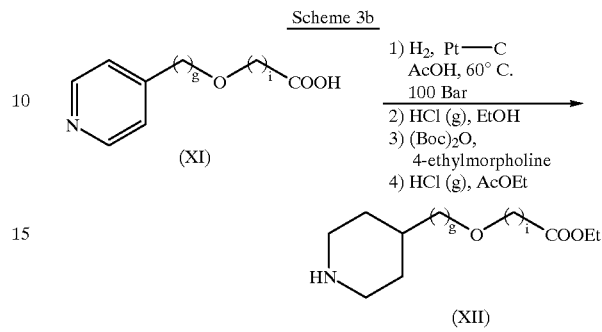

Esterification of the free carboxylic acid is effected according to known methods, for example using hydrochloric acid in an alcohol such as methanol or ethanol.

In a further process variant, an aminocarboxylic acid protected at the nitrogen with e.g. tert.butyloxycaronyl (Boc) or benzyloxycarbonyl (Cbz), such as e.g. N-Boc-piperidine-3-carboxylic acid, can be reacted with another aminocarboxylic acid protected as an ester, such as e.g. ethyl 3-amino-3-phenyl-propionate, or a salt thereof using a coupling reagent such as CDMT under the influence of a base such as N-MM in a solvent such as THF (Scheme 3c).

Scheme 3c

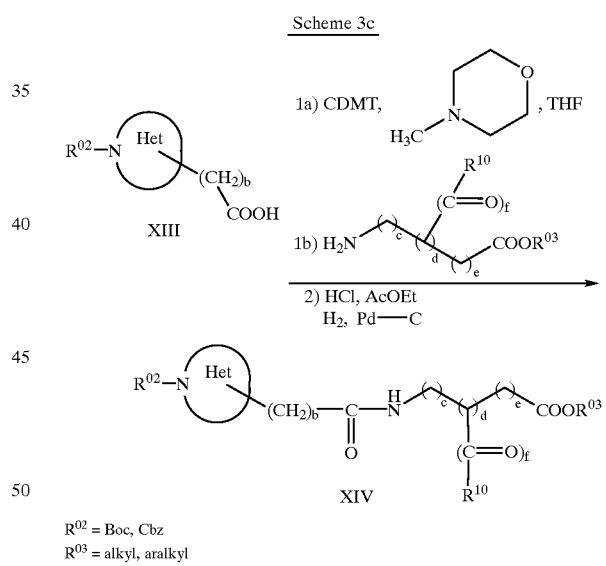

The nitrogen protecting group Boc is then cleaved off using hydrochloric acid in ethyl acetate and the protecting group benzyloxycarbonyl (Cbz) is cleaved off by hydrogenation in ethanol in the presence of Pd/C.

The conversion of a compound of formula I into a pharmaceutical usable salt can be carried by treating such a compound in the usual manner with an inorganic acid, for example a hydrohalic acid, such as, for example, hydrochloric acid or hydrobromic acid, sulphuric acid, nitric acid, phosphoric acid etc., or with an organic acid, such as, for example, acetic acid, citric acid, maleic acid, fumaric acid, tartaric acid, methanesulphonic acid or p-toluenesulphonic acid.

The corresponding carboxylate salts can be manufactured from the compounds of formula I by treatment with physiologically compatible bases.

The conversion of a compound of formula I into a pharmaceutically usable ester can be undertaken by esterifying such as compound in the usual manner or as described in the Examples.

As mentioned previously, the compounds of formula I and their pharmaceutically usable salts and esters inhibit especially the binding of various adhesive proteins such as fibrinogen, vitronectin, von Willebrand factor, fibronectin, thrombospondin and osteopontin to the vitronectin receptors (such as e.g. $\alpha_v\beta_3$, $\alpha_v\beta_5$, $\alpha_v\beta_6$, $\alpha_v\beta_8$, etc.) on the surface of various types of cell. The compounds therefore influence cell-cell and cell-matrix interactions. Since the vitronectin receptors play a role, inter alia, in the spread of tumor cells, in the new growth of vascular tissue, in the degradation of bone tissue, in the migration of smooth muscle cells in vascular walls and in the penetration of virus particles into target cells, the compounds can be used as vitronectin receptor antagonists in the control or prevention-of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi. Since the binding of adhesive proteins to the fibronectin receptor ($\alpha_{IIb}\beta_3$) on the surface of blood platelets is practically not inhibited, undesired side effects such as bleeding can be suppressed with the terapeutic application of the compounds.

The inhibition of the binding of adhesive proteins such as e.g. fibrinogen to vitronectin receptors (such as e.g. $\alpha_v\beta_3$, $\alpha_v\beta_5$, $\alpha_v\beta_6$, $\alpha_v\beta_8$, etc. or to the fibrinogen receptor ($\alpha_{IIb}\beta_3$) by compounds of formula I can be determined as described by L. Alig et al. [*J.Med.Chem.*, 35: 4393–4407 (1992)].

In detail thereto, the wells of microtitre plates (Nunc-lmmunoplate MaxiSorp) were coated overnight at 4° C. with the vitronectin receptor $\alpha_v\beta_3$ (from human placenta, 100 μl/well) in a buffer system with 150 mmol/l NaCl, 1 mmol/ CaCl$_2$, 1 mmol/l MgCl$_2$, 0.0005% Triton X-100 and 20 mmol/l Tris HCl, pH 7.4. The non-specific binding sites were blocked by incubation with 3.5% bovine serum albumin (BSA from Fluka) at 20° C. for at least 1 h. Before the beginning of the test the plates were washed in each case once with 150 mmol NaCl, 1 mmol/l CaCl$_2$, 1 mmol/l MgCl$_2$ and 20 mmol/l Tris HCl, pH 7.4 (buffer A). The thus-coated plates can be stored for at least 2 months in the presence of 0.05% NaN$_3$ (in buffer A) at 4° C. in a humidity chamber without loss of binding activity. Fibrinogen (IMCO, free from fibronectin) was diluted to 1.5 μg/ml in buffer A in the presence of 1% BSA. The wells coated with the receptor were incubated with fibrinogen (100 μl/well) overnight at room temperature in the absence of or in the presence of increasing concentrations of RGDS (as the reference substance) or the compounds to be measured. Non-bound fibrinogen was removed by three-fold washing with buffer A and bound fibrinogen was detected by an ELISA procedure. Antibodies of rabbits directed against human fibrinogen (Dakopatts, Denmark), diluted in buffer A in the presence of 0.1% BSA, were added at room temperature for 1 h., followed by incubation with biotinylated antibodies directed against rabbit immunoglobulin (Amersham) for 30 min. Non-bound antibodies were removed by three-fold washing with buffer A. Thereafter, the pre-formed streptavidin-biotinylated peroxidase complex (Amersham) was added for 30 min. Three-fold washing with buffer A was again carried out. After addition of the peroxidase substrate ABTS (2,2'-azino-bis(3-ethylbenzothiazoline-6-sulphonic acid), Boehringer Mannheim) the enzyme activity was measured with a multichannel photometer (UVmax, Molecular Devices). The difference between total binding activity (in the absence of a test substance) and non-specific binding activity (in the presence of 100 μM RGDS) is taken as the specific binding activity. The concentration of a test substance which is required to inhibit the specific binding activity by 50% was defined as the IC$_{50}$.

The isolation of the receptor a$_v$b$_3$ used in the test can be carried out as follows:

Human placenta is stored at −80° C. immediately after its excision. In order to extract the receptor, each placenta is superficially thawed and cut into narrow strips with a scalpel. The pieces are washed twice with a buffer of 150 mmol/l NaCl, 1 mmol/l CaCl$_2$, 1 mmol/l MgCl$_2$ and 20 mmol/l Tris HCl (pH 7.4). The proteins are extracted at room temperature for one hour with a buffer solution from 1% Triton X-100, 150 mmol/l NaCl, 1 mmol/l CaCl$_2$, 1 mmol/l MgCl$_2$, 20 mmol/l Tris HCl, 0.02% NaN$_3$, 0.5 mmol/l phenylmethane—sulphonyl fluoride, 1 mmol/l leupeptin and 2 mmol/l N-ethylmaleimide (pH 7.4) and filtered through sterile gauze. The filtrate is centrifuged at 30,000 g for 30 min. at 4° C. The glycoproteins are firstly separated with the aid of a concanavalin A-Sepharose 4B column. The proteins bound to the column are eluted and then added to a Aeg-RGDS column. After repeated washing the bound vitronectin receptor is eluted by 3 mmol/l RGDS in a buffer of 0.1% Triton X-100, 150 mmol/l NaCl, 20 mmol/l Tris HCl, 1 mmol/l CaCl$_2$, 1 mmol MgCl$_2$, 0.05% NaN$_3$ (pH 7.0).

The results obtained in the foregoing test using representative compounds of formula as the test compound are compiled in the following Table.

TABLE 1

| Substance | VNR IC$_{50}$ [μM] |
|---|---|
| rac [1-(2-Guanidino-4-propyl-thiazole-5-carbonyl)-piperidin-3-ylmethoxy]-acetic acid | 0.018 |
| (R)-[1-(2-Guanidino-4-methyl-thiazole-5-carbonyl)-piperidin-3-ylmethoxy]-acetic acid | 0.05 |
| rac [1-(4-Cyclopentyl-2-guanidino-thiazole-5-carbonyl)-piperidin-3-ylmethoxy]-acetic acid | 0.09 |
| rac [1-(2-Guanidino-4-methyl-thiazole-5-carbonyl)-piperidin-3-ylmethoxy]-acetic acid | 0.039 |
| rac [1-(2-Guanidino-4-phenyl-thiazole-5-carbonyl)-piperidin-3-ylmethoxy]-acetic acid | 0.07 |
| rac [1-(4-tert-Butyl-2-guanidino-thiazole-5-carbonyl)-piperidin-3-ylmethoxy]-acetic acid | 0.022 |

Preferred compounds have an IC$_{50}$ value which is below 100 μM; especially preferred compounds have a value below 10 μM.

The compounds of formula I and their pharmaceutically usable salts and esters can be used as medicaments (e.g. in the form of pharmaceutical preparations). The pharmaceutical preparations can be administered internally such as orally (e.g. in the form of tablets, coated tablets, dragees, hard and soft gelatine capsules, solutions, emulsions or suspensions), nasally (e.g. in the form of nasal sprays) or rectally (e.g. in the form of suppositories). The administration can, however, also be effected parentally such as intramuscularly or intravenously (e.g. in the form of injection solutions).

The compounds of formula I and their pharmaceutically usable salts and esters can be processed with pharmaceutically inert, inorganic or organic adjuvants for the production of tablets, coated tablets, dragees and hard gelatine capsules. Lactose, corn starch or derivatives thereof, talc, stearic acid or its salts etc. can be used, for example, as such adjuvants for tablets, dragees and hard gelatine capsules.

Suitable adjuvant for soft gelatine capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutical usable salts and esters can be used as vitronectin receptor angatonists, especially for the treatment or propylaxis of neoplasms, tumor metastasing, osteoporosis, Paget's disease, diabetic retinopathy, macular degeneration, restenosis following vascular intervention, psoriasis, arthritis, kidney failure as well as infections caused by viruses, bacteria or fungi. The dosage can vary in wide limits and will, of course by fitted to the individual requirements in each particular case. In the case of oral administration a daily dosage of about 0.1 mg to 20 mg per kg body weight, preferably about 0.5 mg to about 4 mg per kg body weight (e.g. approximately 300 mg per person), divided into preferably 1–3 individual doses, which can consist, for example, of the same amounts, should in general be adequate. It will, however, be clear that the upper limit given above can be exceeded when it is established that this is indicated.

The invention is illustrated in the following by Examples, with the Examples having no limiting character.

EXAMPLES

| List of common abbreviations | |
|---|---|
| AcOEt | ethyl acetate |
| AcOH | acetic acid |
| Aeg-RGDS | aminoethylglycine—Arg—Gly—Asp—Ser—OH |
| Boc | tert-butoxycarbonyl |
| BOP | (benzotriazol-1-yloxy)-tris-(dimethylamino)-phosphonium hexafluorophosphate |
| BSA | bovine serum albumin |
| Cbz | benzyloxycarbonyl |
| CDMT | 2-chloro-4,6-dimethoxy-1,3,5-triazine |
| DMF | dimethylformamide |
| EDC | N-(3-dimethylaminopropyl)-N'-ethyl-carbodiimide hydrochloride |
| EI | electron impact |
| ELISA | enzyme-linked immunosorbent assay |
| EtOH | ethanol |
| FAB | fast atom bombardment |
| HBTU | O—(benzotriazol-1-yl)-N,N,N',N'-tetramethyluronium hexafluorophosphate |
| ISP | ion spray (positively charged ions) |
| MeCN | acetonitrile |
| MeOH | methanol |
| MS | mass spectroscopy |

| List of common abbreviations | |
|---|---|
| N-MM | N-methylmorpholine |
| RGDS | H—Arg—Gly—Asp—Ser—OH |
| RP | reverse phase |
| RT | room temperature |
| m.p. | melting point |
| t-BuOH | tert-butanol |
| TFA | trifluoroacetic acid |

Example 1

13.9 ml of ethyl bromopyruvate are added to a solution of 11.81 g of 2-imino-4-thiobiuret (Aldrich) in 100 ml of ethanol and the reaction mixture is heated under reflux for 3 hours (J. Med. Chem. 34, 914–918 (1991)). Subsequently, the mixture is cooled to room temperature and the reaction product is precipitated by the addition of 550 ml of ethyl acetate and filtered off. There are obtained 14.6 g of yellowish ethyl 2-guanidino-thiazole-4-carboxylate hydrobromide. MS: 214 $(M)^+$.

Example 2 a) 1.62 ml of bromine are added dropwise within 10 minutes while stirring and cooling at 0–5° C. to a 2-phase mixture of 5.06 ml of ethyl butyrylacetate and 14.4 ml of water [*J. Med. Chem.*, 34: 914–918 (1991)]. The mixture is stirred for a further 30 minutes at 0° C. and then the product is extracted with ether. After drying there are obtained 7.6 g of crude bromoketone, which is used immediately in Example 3.

b) Analogously to the procedure of Example 2a, using ethyl benzoylacetate or ethyl pivaloylacetate or ethyl cyclopentylcarbonylacetate in place of ethyl butyrylacetate there is prepared the corresponding bromoketone.

Example 3

Analogously to the procedure of Example 1, using ethyl 2-chloroaceto-acetate or the bromoketones prepared under Example 2 in place of ethyl bromopyruvate there are prepared the following compounds:
a) Ethyl 2-guanidino-4-methyl-thiazole-5-carboxylate hydrochloride, MS: 228 $(M^+)$,
b) ethyl 2-guanidino-4-propyl-thiazole-5-carboxylate hydrobromide, MS: 256 $(M^+)$,
c) ethyl 2-guanidino-4-phenyl-thiazole-5-carboxylate hydrobromide, MS: 290 $(M^+)$,
d) ethyl 4-tert-butyl-2-guanidino-thiazole-5-carboxylate hydrobromide, MS: 271 $(M+H)^+$,
e) ethyl 4-cyclopentyl-2-guanidino-thiazole-5-carboxylate hydrobromide, MS: 283 $(M+H)^+$.

Example 4

220 mg of 2-guanidino-4-methyl-thiazole-5-carboxylic acid, 265 mg of ethyl (RS)-3-[(piperidine-3-carbonyl)-amino]-propionate hydrochloride, 3 ml of DMF, 0.34 ml of N-methylmorpholine (N-MM) and 569 mg of O-(benzotriazol-1-yl)-N,N,N',N'-tetramethyluronium hexafluorophosphate (HBTU) are stirred at RT for 22 hours. The reaction mixture is diluted with ethyl acetate and washed firstly with a dilute aqueous solution of sodium carbonate and sodium chloride, then with dilute sodium chloride solution and finally with saturated sodium chloride solution. The organic phase is dried over sodium sulphate and evaporated in a vacuum. Chromatography on silica gel with ethyl acetate: ethanol 5:1 gives 270 mg of ethyl (RS)-3-[[1-(2-guanidino-4-methyl-thiazole-5-carbonyl)-piperidine-3-carbonyl]-amino]-propionate as a pale yellow foam. MS: 411 (M+H)$^+$.

The starting materials can be prepared as follows:

a) 4.59 g of (RS)-piperidine-1,3-dicarboxylic acid 1-tert.-butyl ester, 3.51 g of 2-chloro4,6-dimethoxy-[1,3,5]-triazine (CDMT), 60 ml of THF and 2.25 ml of N-MM are stirred under argon at 0° C. for 3 hrs. After the addition of 3.07 g of β-alanine ethyl ester hydrochloride and 2.25 ml of N-MM the mixture is stirred at RT for 18 hrs. The reaction mixture is diluted with ethyl acetate and washed in sequence with ice-cold dilute hydrochloric acid, water, dilute sodium carbonate solution, water and saturated sodium chloride solution. After drying over sodium sulphate and evaporation of the solvent there are obtained 6.16 g of (RS)-3-(2-ethoxycarbonyl-ethylcarbamoyl)-piperidine-1-carboxylic acid tert.-butyl ester as a pale yellow oil. MS: 329 (M+H)$^+$.

b) 985 mg of (RS)-3-(2-ethoxycarbonyl)-ethylcarbamoyl)-piperidine-1-carboxylic acid tert.-butyl ester are dissolved in 4.5 ml of ethyl acetate, treated with 4.5 ml of 4N HCl in ethyl acetate and stirred at RT for 1 hr. After evaporation of the solvent in a vacuum there are obtained 803 mg of ethyl (RS)-3-[(piperidine-3-carbonyl)-amino]-proponate hydrochloride (1:1), m.p. 105–108° C., MS: 299 (M+H)$^+$.

c) 2.65 g of ethyl 2-guanidino-4-methyl-thiazole-5-carboxylate hydrochloride (prepared according to Example 3) are heated to 75° C. for 7 hrs. in 70 ml of ethanol and 11 ml of 2N NaOH. The reaction mixture is evaporated to dryness in a vacuum. The residue is taken up in 40 ml of ethanol, the solution is filtered clear and the product is precipitated with 2 ml of acetic acid. There are obtained 1.82 g of 2-guanidino-4-methyl-thiazole-5-carboxylic acid of m.p. 1 96° C.

Example 5

103 mg of ethyl (RS)-3-[[1-(2-guanidino-4-methyl-thiazole-5-carbonyl)-piperidine-3-carbonyl]-amino]-propionate are left to stand at RT in 2.1 ml of 25 percent hydrochloric acid for 6 hrs. The solution is evaporated and the residue is taken up in water and again evaporated. There are obtained 92 mg of (RS)-3-[[1-(2-guanidino-4-methyl-thiazole-5-carbonyl)-piperidine-3-carbonyl]-amino]-propionic acid hydrochloride (1:2) as a white foam, MS: 383 (M+H)$^+$.

Example 6

154 mg of tert.-butyl [1-(2-guanidino-4-methyl-thiazole-5-carbonyl)-piperidine-4-yloxy]-acetate are dissolved in 1.5 ml of dichloromethane and treated with 1.5 ml of trifluoroacetic acid. After 2 hrs. the mixture is evaporated in a vacuum. The residue is dissolved in water and the solution is again evaporated. There are obtained 209 g of mg [1-(2-guanidino-4-methyl-thiazole-5-carbonyl)-piperidine-4-yloxy]-acetic acid trifluoro- acetate (1:2) as a light hygroscopic foam, MS: 342 (M+H)$^+$.

The starting material (m.p. 205° C., MS: 398 (M+H)$^+$) is obtained by coupling 2-guanidino-4-methyl-thiazole-5-carboxylic acid with tert.-butyl (piperidin-4-yloxy)-acetate according to the method given in Example 4.

Example 7

In analogy to Example 4, by coupling 2-guanidino-thiazole-4-carboxylic acid sodium salt with ethyl (RS)-3-[(piperidine-3-carbonyl)-amino]-propionate hydrochloride there is obtained ethyl (RS)-3-[[1-(2-guanidino-thiazole-4-carbonyl)-piperidine-3-carbonyl]-amino]-propionate as a white foam. MS: 397 (M+H)$^+$.

Example 8

Analogously to Example 5, from ethyl (RS)-3-[[1-(2-guanidino-thiazole-4-carbonyl)-piperidine-3-carbonyl]-amino]-propionate there is obtained (RS)-3-[[1-(2-guanidino-thiazole-4-carbonyl)-piperidine-3-carbonyl]-amino]-propionic acid as the hydrochloride. This is neutralized in water with NH$_3$ and purified on Kieselgel 100 C$_{18}$-reverse phase. There is obtained (RS)-3-[[1-(2-guanidino-thiazole-4-carbonyl)-piperidine-3-carbonyl]-amino]-propionic acid as a white foam, MS: 369 (M+H)$^+$.

Example 9

140 mg of tert.-butyl (R)-[1-(2-guanidino-4-methyl-thiazole-5-carbonyl)-pyrrolidin-3-ylmethoxy]-acetate are reacted as in Example 6. The crude trifluoroacetate is dissolved in water, neutralized with dilute NH$_3$, purified on Kieselgel 100 C$_{18}$-reverse phase and lyophilized from water. There are obtained 99 mg of (R)-[1-(2-guanidino-4-methyl-thiazole-5-carbonyl)-pyrrolidin-3-ylmethoxy]-acetic acid, m.p. 136° C. (sintering), [α]$_D$=+14.2°, (H$_2$O, c=0.5), MS: 342 (M+H)$^+$.

a) 20 mg of tetrabutylammonium bromide in 1 ml of water and then within 5 min. 20 g of 50% NaOH in water are added dropwise to a mixture of 2.05 g of (R)-1-[(R)-α-methylbenzyl]-3-pyrrolidinemethanol, 25 ml of toluene and 2.2 ml of tert.-butyl bromoacetate while stirring vigorously. After 6.5 hrs. the mixture is diluted with toluene, washed neutral with water, dried and evaporated in a vacuum. Chromatography on silica gel gives 2.1 g of tert.-butyl (R)-[1-(R)-[1-phenyl-ethyl]-pyrrolidin-3-ylmethoxy]-acetate, [α]$_D$=+29.2°, (MeOH, c=1.0), MS: 319 (M)$^+$.

b) By catalytic hydrogenation on Pd/C in EtOH there is obtained therefrom tert.-butyl (R)-(pyrrolidin-3-ylmethoxy)-acetate, MS: 216 (M+H)$^+$.

c) By coupling 2-guanidino-4-methyl-thiazole-5-carboxylic acid with tert.-butyl (R)-(pyrrolidin-3-ylmethoxy)-acetate according to the method given in Example 4 there is obtained tert.-butyl (R)-[1-(2-guanidino-4-methyl-thiazole-5-carbonyl)-pyrrolidin-3-ylmethoxy]-acetate as a pale yellow resinous foam, [α]$_D$=+3.2°, (MeOH, c=0.5), MS: 398 (M+H)$^+$.

Example 10

Analogously to Example 9 there is prepared (S)-[1-(2-guanidino-4-methyl-thiazole-5-carbonyl)-pyrrolidin-3-ylmethoxy]-acetic acid; m.p. 139° C. (sintering), [α]$_D$=−13.6°, (H$_2$O, c=0.5), MS: 342 (M+H)$^+$.

In addition, the following intermediates are prepared analogously:

a) tert.-Butyl (S)-[1-(R)-[1-phenyl-ethyl]-pyrrolidin-3-ylmethoxy]-acetate, [α]$_D$=+42.7°, (MeOH, c=1.0), MS: 319 (M)$^+$.

b) tert.-Butyl (S)-(pyrrolidin-3-ylmethoxy)-acetate, MS: 216 (M+H)$^+$.

c) tert.-Butyl (S)-[1-(2-guanidino-4-methyl-thiazole-5-carbonyl)-pyrrolidin-3-ylmethoxy]-acetate, pale yellow resinous foam, [α]$_D$=−2.4°, (MeOH, c=0.5), MS: 398 (M+H)$^+$.

Example 11

In the same manner as described in Example 4, from 2-guanidino-thiazole-5-carboxylic acid and ethyl (RS)-

(piperidin-3-ylmethoxy)-acetate hydrochloride there is obtained ethyl (RS)-[1-(2-guanidino-thiazole-5-carbonyl)-piperidin-3-ylmethoxy]-acetate, m.p. 156° C., MS: 370 (M+H)$^+$.

2-Guanidino-thiazole-5-carboxylic acid is obtained from ethyl 2-guanidino-thiazole-5-carboxylate by saponification with sodium hydroxide solution in alcohol, dilution with water and precipitation with hydrochloric acid at pH 3, m.p. 219° C.

Example 12

Analogously to Example 5, from ethyl (RS)-[1-(2-guanidino-thiazole-5-carbonyl)-piperidin-3-ylmethoxy]-acetate after evaporation of the reaction solution and trituration of the residue in ether there is obtained (RS)-[1-(2-guanidino-thiazole-5-carbonyl)-piperidin-3-ylmethoxy]-acetate hydrochloride (1:1), m.p. 75° C. (dec.), MS: 342 (M+H)$^+$.

Example 13

In analogy to Example 4, from 2-guanidino-4-methyl-thiazole-5-carboxylic acid and ethyl (RS)-3-phenyl-3-[(RS)-(piperidin-3-carbonyl)-amino]-propionate hydrochloride after chromatography on silica gel with dichloromethane:ethanol there is obtained a mixture of ethyl (RS)- and (SR)-3-[[(RS)-1-(2-guanidino-4-methyl-thiazole-5-carbonyl)-piperidine-3-carbonyl]-amino]-3-phenyl-propionate as a pale yellow foam, MS: 487 (M+H)$^+$.

The starting material can be prepared as follows:

a) In analogy to Example 4a, from (RS)-piperidine-1,3-dicarboxylic acid 1-tert.-butyl ester and ethyl (RS)-3-amino-3-phenyl-propionate hydrochloride there is obtained tert.-butyl 3-(2-ethoxycarbonyl-1-phenyl-ethylcarbamoyl)-piperidine-1-carboxylate as a mixture of diastereomers, MS: 405 (M+H).

b) As given in Example 4b, there is obtained therefrom ethyl (RS)-3-phenyl-3-[(RS)-(piperidine-3-carbonyl)-amino]-propionate hydrochloride (1:1), MS: 304 (M)$^+$.

Example 14

243 mg of a mixture of ethyl (RS)- and (SR)-3-[[(RS)-1-(2-guanidino-4-methyl-thiazole-5-carbonyl)-piperidine-3-carbonyl]-amino]-3-phenyl-propionate are left to stand in 5 ml of 25% hydrochloric acid at RT for 24 hrs. The solution is evaporated, the residue is dissolved in water and the solution is adjusted to pH 8 with ammonia. The precipitate is filtered off under suction and purified by repeated trituration in water. There are obtained 77 g of a mixture of (RS)- and (SR)-3-[[(RS)-1-(2-guanidino-4-methyl-thiazole-5-carbonyl)-piperidine-3-carbonyl]-amino]-3-phenyl-propionic acid, m.p. 174° C., MS: 459 (M+H)$^+$.

Example 15

146 ml of 3N sodium hydroxide solution are added to 14.6 g of the ester obtained under Example 1 and the reaction mixture is boiled under reflux for 3 hours [J. Med. Chem. 34: 914–918 (1991)]. Then, the reaction mixture is cooled to RT, acidified with 73 ml of 6N hydrochloric acid and evaporated to ¼ of the volume. The precipitated material is filtered off and washed with water. After drying there are obtained 9.44 g of beige 2-guanidino-thiazole-4-carboxylic acid hydrochloride. MS: 186 (M)$^+$.

Example 16

Analogously to the process in Example 15, from the esters obtained according to Example 3 there are prepared the following compounds:

a) 2-Guanidino-4-methyl-thiazole-5-carboxylic acid, MS: 200 (M+), b) 2-guanidino-4-propyl-thiazole-5-carboxylic acid hydrochloride, MS: 229 (M+H)$^+$, c) 2-guanidino-4-phenyl-thiazole-5-carboxylic acid, MS: 263 (M+H)$^+$, d) 4-tert-butyl-2-guanidino-thiazole-5-carboxylic acid hydrochloride, MS: 243 (M+H)$^+$, e) 4-cyclopentyl-2-guanidino-thiazole-5-carboxylic acid hydrochloride, MS: 255 (M+H)$^+$.

Example 17 a) 4.05 ml of benzyl isocyanate are added to a solution of 5.0 g of ethyl 2-amino-4-methyl-thiazole-5-carboxylate in 50 ml of DMF. The reaction mixture is stirred at RT overnight, evaporated on a rotary evaporator and the residue is suspended in methylene chloride:methanol 1:1. The insoluble material is filtered off and dried. There are obtained 4.6 g of colorless ethyl 2-(3-benzyl-ureido)-4-methyl-thiazole-5-carboxylate, MS: 320 (M+H)$^+$.

b) A suspension of 3.6 g of the ester obtained under a) in 36 ml of ethanol is treated with 68 ml of 1 N sodium hydroxide solution and boiled at reflux for 8 hours. Subsequently, the reaction mixture is poured into 70 ml of 1 N ice-cold hydrochloric acid and the solution is evaporated to half of the volume. After cooling the separated crystals are filtered off and dried. There are thus obtained 2.25 g of colorless 2-(3-benzyl-ureido)4-methyl-thiazole-5-carboxylic acid. MS: 292 (M+H)$^+$.

Example 18

200 ml of 50% sodium hydroxide solution and 1 g of butylammonium hydrogen sulphate are added to a solution of 21.5 g of tert-butyl rac 3-hydroxymethyl-piperidine-1-carboxylate [K. Hilpert et al., J. Med. Chem., 37: 3889 (1994); EP 0 468 231] in 200 ml of toluene. The 2-phase mixture is cooled to 15° C. and treated with 30 ml of ethyl bromoacetate while stirring vigorously. After stirring at room temperature for 2.5 hours the reaction mixture is poured on to ice-water and extracted twice with ether. The organic phases are washed 4 times with water. The combined aqueous phases are acidified with concentrated hydrochloric acid and extracted twice with ethyl acetate. The ethyl acetate phases are washed with sodium chloride solution, dried and evaporated. There are obtained 18.3 g of tert-butyl rac-3-carboxymethoxymethyl-piperidine-1-carboxylate as a yellow oil, MS: 273 (M)$^+$.

b) Hydrogen chloride is conducted for 10 minutes at 0° C. into a solution of 18.3 g of the material obtained under a) in 183 ml of ethanol. Then, the reaction mixture is stirred at 0° C. for a further 2 hours, then evaporated on a rotary evaporator and the residue is dried. There are obtained 9.6 g of pale beige crystalline ethyl rac (piperidin-3-ylmethoxy)-acetate hydrochloride. MS: 202 (M+H)$^+$.

Example 19 a) The following compounds are prepared analogously to the procedure in Example 18a, but using a) tert-butyl (S)-3-hydroxymethyl-piperidine-1-carboxylate or b) tert-butyl (R)-3-hydroxymethyl-piperidine-1-carboxylate or c) rac-Boc-prolinol (EP 0 468 231) in place of tert-butyl rac 3-hydroxymethyl-piperidine-1-carboxylate:

a1) tert-Butyl (S)-3-carboxymethoxymethyl-piperidine-1-carboxylate, MS: 273 (M)$^+$, b1) tert-butyl (R)-3-carboxymethoxymethyl-piperidine-1-carboxylate, MS: 273 (M)$^+$, c1) tert-butyl rac 2-carboxymethoxymethyl-pyrrolidine-1-carboxylate, MS: 260 (M+H)+,
b) from the products a1, b1, c1 there are prepared analogously to the procedure in Example 18b the corresponding amino ester hydrochlorides a2), b2), c2), which are used immediately.

Example 20 a) Analogously to the procedure described in Example 18a, but using ethyl bromopropionate in place of ethyl bromoacetate there is obtained tert-butyl rac 3-(2-ethoxycarbonyl-ethoxymethyl)-piperidine-1-carboxylate, MS: 316 (M+H)+,
b) Analogously to the procedure described in Example 18b), but using the products obtained according to Example 20a) there is obtained the corresponding free amine hydrochloride, which is used directly.

Example 21 a) Analogously to the procedure described in Example 18a, but using rac 4-phenylmethyl-2-morpholine-methanol in place of tert-butyl 3-hydroxymethyl-piperidine-1-carboxylate there is obtained ethyl rac (4-benzyl-morpholin-2-ylmethoxy)-acetate. MS: 294 (M+H)+.

b) 1.0 g of the ester obtained under a) is dissolved in 10 ml of ethanol, treated with 3.4 ml of 1 N hydrochloric acid and 0.1 g of palladium-on-charcoal and hydrogenated. After removal of the catalyst by filtration and evaporation of the filtrate there is obtained 0.8 g of ethyl rac (morpholin-2-ylmethoxy)-acetate hydrochloride, which is used immediately. MS: 204 (M+H)+.

Example 22 a) A solution of 20.0 g of 4-pyridinylmethoxyacetic acid in 200 ml of acetic acid is treated with 2 g of platinum-on-charcoal and hydrogenated for 24 hours at 60° C. under 100 bar of hydrogen. The catalyst is filtered off and the filtrate is evaporated. 24.5 g of residue are thus obtained.

b) Hydrochloric acid gas is conducted into a solution of the residue obtained under a) in 245 of ethanol at 0° C. for 10 minutes. Then, the reaction mixture is stirred at 0° C. for a further 2 hours, subsequently evaporated on a rotary evaporator and the residue is dried. 24.0 g of brown oil are obtained.

c) A solution of the product obtained under b) in 240 ml of dioxan is treated with 25.2 ml of 4-ethylmorpholine and a solution of 22.9 g of di-t-butyl dicarbonate in 50 ml of dioxan and stirred at RT overnight. The reaction mixture is evaporated, the residue is taken up in ethyl acetate and shaken once with 5% potassium hydrogen sulphate:10% potassium sulphate solution and twice with water. The organic phase is dried and evaporated and the residue is chromatographed on silica gel with hexane:ethyl acetate 4:1. 6.4 g of tert-butyl 4-ethoxycarbonylmethoxymethyl-piperidine-1-carboxylate are thus obtained. MS: 301 (M)+.

d) The product obtained under c) is reacted analogously to the procedure described in Example 18b. There are thus obtained 5.4 g of ethyl (piperidin-4-ylmethoxy)-acetate, MS: 202 (M+H)+.

Example 23

Analogously to Example 18, but using tert-butyl rac 3-hydroxy-piperidine-1-carboxylate in place of tert-butyl 3-hydroxymethyl-piperidine-1-carboxylate there are obtained the following two products:

a) tert-butyl rac 3-carboxymethoxy-piperidine-1-carboxylate, MS: 260 (M+H)+,
b) ethyl rac (piperidin-3-yloxy)-acetate hydrochloride, MS: 188 (M+H)+.

Example 24

0.9 g of ethyl rac (piperidin-3-ylmethoxy)-acetate hydrochloride (Example 18b) is dissolved in 20 ml in dimethylformamide, treated with 2.18 ml of 4-ethylmorpholine, 1.0 g of the acid from Example 16e) and 1.52 g of benzotriazol-1-yloxy-tris(dimethylamino) phosphonium hexafluorophosphate (BOP). The reaction mixture is stirred at room temperature overnight and then evaporated on a on a rotary evaporator. The residue is chromatographed on a RP-18 column with a water:acetonitrile gradient. There is thus obtained 0.6 g of crystalline ethyl rac [1-(4-cyclopentyl-2-guanidino-thiazole-5-ylcarbonyl)- piperidin-3-ylmethoxy]-acetate. MS: 438(M+J)+.

Example 25

The following compounds were prepared analogously to Example 24 using the hydrochloride from Example 18 and the acids from Example 15 and Example 16:
a) Ethyl rac [1-(2-guanidino-thiazole-4-carbonyl)-piperidin-3-ylmethoxy]-acetate, MS: 370 (M+H)+,
b) ethyl rac [1-(2-guanidino-4-methyl-thiazole-5-carbonyl)-piperidin-3-ylmethoxy]-acetate hexafluorophosphate, MS: 384 (M+H)+,
c) ethyl rac [1-(2-guanidino-4-propyl-thiazole-5-carbonyl)-piperidin-3-ylmethoxy]-acetate, MS: 412 (M+H)+,
d) ethyl rac [1-(2-guanidino-4-phenyl-thiazole-5-carbonyl)-piperidin-3-ylmethoxy]acetate, MS: 446 (M+H)+,
e) ethyl rac [1-(4-tert-butyl-2-guanidino-thiazole-5-carbonyl)-piperidin-3-ylmethoxy]-acetate, MS: 426 (M+H)+.

Example 26

0.35 g of the ester obtained under Example 24 is suspended in 3.5 mol of tetrahydrofuran and treated with 2.4 ml of a 1 N aqeuous hydroxide solution. The mixture is stirred at room temperature for 2 hours, neutralized by the addition of 2.4 ml of 1 N hydrochloric acid and evaporated on a rotary evaporator. After chromatography of the residue on a RP-18 column with a water:acetonitrile gradient there is obtained 0.32 g of colorless crystalline rac [1-(4-cyclopentyl-2-guanidino-thiazol-5-ylcarbonyl)-piperidin-3-ylmethoxy]-acetic acid. MS: 410 (M+H)+.

Example 27

The following products are obtained analogously to Example 26, but using the esters from Example 25:
a) rac [1-(2-Guanidino-thiazole-4-carbonyl)-piperidin-3-ylmethoxy]-acetic acid, MS: 342 (M+H),
b) rac [1-(2-guanidino-4-methyl-thiazole-5-carbonyl)-piperidin-3-ylmethoxy]-acetic acid, MS: 356 (M+H)+,
c) rac [1-(2-guanidino-4-propyl-thiazole-5-carbonyl)-piperidin-3-ylmethoxy]-acetic acid, MS: 384 (M+H)+,
d) rac [1-(2-guanidino-4-phenyl-thiazole-5-carbonyl)-piperidin-3-ylmethoxy]-acetic acid, MS: 418 (M+H)+,
e) rac [1-(4-tert-butyl-2-guanidino-thiazole-5-carbonyl)-piperidin-3-ylmethoxy]-acetic acid, MS: 398 (M+H)+.

Example 28

The following compounds are prepared analogously to Example 24 using the hydrochlorides from Example 19 a2), b2), c2) and, respectively, Example 20 or Example 21b or Example 22d and the acid from Example 16a:
a) Ethyl (S)-[1-(2-guanidino-4-methyl-thiazole-5-carbonyl)-piperidin-3-ylmethoxy]-acetate, MS: 384 (M+H)$^+$,
b) ethyl (R)-[1-(2-guanidino-4-methyl-thiazole-5-carbonyl)-piperidin-3-ylmethoxy]-acetate, MS: 384 (M+H)$^+$,
c) ethyl rac [1-(2-guanidino-4-methyl-thiazole-5-carbonyl)-pyrrolidin-2-ylmethoxy]-acetate, MS: 370 (M+H)$^+$,
d) ethyl rac 3-[1-(2-guanidino-4-methyl-thiazole-5-carbonyl)-piperidin-3-ylmethoxy]-propionate, MS: 398 (M+H)$^+$,
e) ethyl rac [4-(2-guanidino-4-methyl-thiazole-5-carbonyl)-morpholin-2-ylmethoxy]-acetate, MS: 386 (M+H)$^+$,
d) ethyl [1-(2-guanidino-4-methyl-thiazole-5-carbonyl)-piperidin-4-ylmethoxy]-acetate, MS: 384 (M+H)$^+$.

Example 29

The following products are obtained analogously to Example 26, but using the esters from Example 28:
a) (S)-[1-(2-Guanidino-4-methyl-thiazole-5-carbonyl)-piperidin-3-yl-methoxy]-acetic acid, MS: 356 (M+H)$^+$,
b) (R)-[1-(2-guanidino-4-methyl-thiazole-5-carbonyl)-piperidin-3-yl-methoxy]-acetic acid, MS: 356 (M+H)$^+$,
c) rac [1-(2-guanidino-4-methyl-thiazole-5-carbonyl)-pyrrolidin-2-ylmethoxy]-acetic acid, MS: 342 (M+H)$^+$,
d) rac 3-[1-(2-guanidino-4-methyl-thiazole-5-carbonyl)-piperidin-3-ylmethoxy]-propionsaure, MS: 370 (M+H)$^+$,
e) rac [4-(2-guanidino-4-methyl-thiazole-5-carbonyl)-morpholin-2-ylmethoxy]-acetic acid, MS: 358 (M+H)$^+$,
f) ethyl [1-(2-guanidino-4-methyl-thiazole-5-carbonyl)-piperidin-4-ylmethoxy]-acetate, MS: 356 (M+H)$^+$.

Example 30

Analogously to Example 24, but using the amine from Example 18 b) and the acid from Example 17 b) in place of the acid from Example 15 there is obtained ethyl rac [1-[2-(3-benzyl-ureido)4-methyl-thiazole-5-carbonyl]-piperidin-3-ylmethoxy]-acetate, MS: 475 (M+H)$^+$.

Example 31

The following acid is obtained analogously to Example 26, but using the ester from Example 30:
rac [1-[2-(3-Benzyl-ureido)4-methyl-thiazole-5-carbonyl]-piperidin-3-ylmethoxy]-acetic acid, MS: 447 (M+H)$^+$.

Example 32

Analogously to Example 24, but using the amine from Example 22d there is obtained
ethyl [1-(2-guanidino-thiazole-4-carbonyl)-piperidin-4-ylmethoxy]-acetate, MS: 370 (M+H)$^+$.

Example 33

Analogously to Example 24, but using the hydrochloride from Example 23 and the acid from Example 16a there is obtained
ethyl rac [1-(2-guanidino-4-methyl-thiazole-5-carbonyl)-piperidin-3-yloxy]-acetate, MS: 370 (M+H)$^+$.

Example 34

Analogously to Example 24, but using the acid from Example 35 and the hydrochloride from Example 18b there is obtained
ethyl rac [1-[4-methyl-2-(3-methyl-ureido)-thiazole-5-carbonyl]-piperidin-3-ylmethoxy]-acetate, MS: 398 (M)$^+$.

Example 35

Ethyl 4-methyl-2-[[(methylamino)carbonyl]amino]-thiazole-5-carboxylate is hydrolyzed to the corresponding 4-methyl-2-(3-methyl-ureido)-thiazole-5-carboxylic acid, MS: 214 (M-H)$^-$, analogously to Example 15.

Example 36

The following products are obtained analogously to Example 26, but using the ester from Example 32 or Example 33 or Example 34:
a) [1-(2-Guanidino-thiazole-4-carbonyl)-piperidin-4-ylmethoxy]-acetic acid, MS: 342 (M+H)$^+$,
b) rac [1-(2-guanidino-4-methyl-thiazole-5-carbonyl)-piperidin-3-yloxy]-acetic acid, MS: 342 (M+H)$^+$,
c) rac [1-[4-methyl-2-(3-methyl-ureido)-thiazole-5-carbonyl]-piperidin-3-ylmethoxy]-acetic acid, MS: 371 (M+H)$^+$.

Example A

A compound of formula I can be used as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Upon reading the present specification various alternative embodiments will become obvious to the skilled artisan. These variations are to be considered within the scope and spirit of the subject invention which is only to be limited by the claims that follow and their equivalents.

What is claimed is:
1. A compound of the formula:

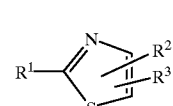

(I)

wherein
R¹ is

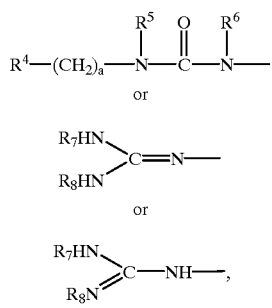

R² is

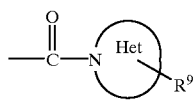

in which Het is a 5- to 8-atom heterocyclic ring that is substituted with R⁹, the heterocyclic ring contains the depicted nitrogen atom and one atom selected from the group consisting of C, O, N, and S, with the remaining atoms in the heterocyclic ring being C;

R³ is hydrogen, alkyl, cycloalkyl, aryl, aralkyl, or heteroaryl;

R⁴ is hydrogen, alkyl, cycloalkyl, aryl or, heteroaryl;

R⁵, R⁶, R⁷ and R⁸ are each independently hydrogen, alkyl, or cycloalkyl, or R⁷ and R⁸ together with the N atoms to which they are attached form a 5- to 8-membered heterocyclic ring or 5- to 8-membered heterocyclic ring that is substituted with alkyl;

R⁹ is

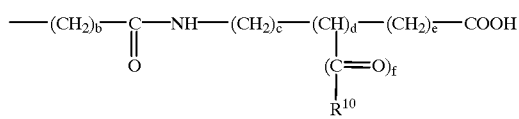

or —(CH₂)$_g$—(O)$_h$—(CH₂)—COOH,

R¹⁰ is aryl, aralkyl, heterocyclyl, or an α-amino acid bonded via the amino group;

a, b, and c are each independently integers from 0 to 4, d is 0 or 1, e is an integer from 0 to 4, when d is 0 then f is 0, the sum of c, d and e is an integer from 1 to 4, f is O or 1, g is an integer from 0 to 5, h is 0 or 1, when h is 1 i is not 0, the sum of g, h and i is an integer from 2 to 5;

or a pharmaceutically usable salt or ester thereof.

2. The compound in accordance with claim 1, wherein R² is bonded to position 5 and R³ is bonded to position 4 of the thiazole ring.

3. The compound in accordance with claim 2, wherein Het in R² is a 5- or 6-membered heterocyclic ring.

4. The compound in accordance with claim 3, wherein Het in R² contains an O atom in the heterocyclic ring.

5. The compound in accordance with claim 2, wherein Het in R² is a pyrrolidine, piperidine, or morpholine ring.

6. The compound in accordance with claim 5, wherein Het in R² is a pyrrolidine ring substituted with R⁹ in the 2- or 3-position, a piperidine ring substituted with R⁹ in the 3- or 4-position, or a morpholine ring substituted with R⁹ in the 2- or 3- position.

7. The compound in accordance with claim 1, wherein R³ is hydrogen, alkyl, cycloalkyl, phenyl, or phenyl substituted with one or more substituents selected from the group consisting of alkyl, alkoxy, halogen, hydroxy, and amino.

8. The compound in accordance with claim 1, wherein R⁴ is hydrogen, alkyl, cycloalkyl, phenyl, or phenyl substituted with one or more substituents selected from the group consisting of alkyl, alkoxy, halogen, hydroxy, and amino.

9. The compound in accordance with claim 1, wherein R⁵, R⁶, R⁷ and R⁸ are hydrogen or R⁵ and R⁶ are each hydrogen and R⁷ and R⁸ together with the N atoms to which they are attached form a 5- or 6-membered heterocyclic ring.

10. The compound in accordance with claim 9, wherein R⁵, R⁶, R⁷ and R⁸ are hydrogen.

11. The compound in accordance with claim 1, wherein R¹⁰ is phenyl, pyridyl, phenyl substituted with one or more substituents selected from the group consisting of alkyl, alkoxy, halogen, hydroxy and amino, or pyridyl substituted with one or more substituents selected from the group consisting of alkyl, alkoxy, halogen, hydroxy and amino.

12. The compound in accordance with claim 11, wherein R¹⁰ is phenyl and f is 0.

13. The compound in accordance with claim 1, wherein the compound has the formula:

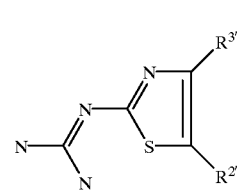

Ia wherein
R² is

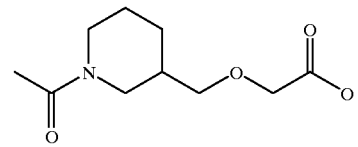

and
R³ is alkyl, cycloalkyl, or phenyl.

14. The compound in accordance with claim 13, wherein R³ is cycloalkyl.

15. The compound in accordance with claim 14, wherein the compound of formula la is rac [1-(4-cyclopentyl-2-guanidino-thiazol-5-ylcarbonyl)-piperidin-3-ylmethoxy]-acetic acid.

16. The compound in accordance with claim 13, wherein R³' is alkyl.

17. The compound in accordance with claim 16, wherein the compound of formula la is rac [1-(2-guanidino-4-methyl-thiazole-5-carbonyl)-piperidin-3-ylmethoxy]-acetic acid.

18. The compound in accordance with claim 16, wherein the compound of formula la is rac [1-(2-guanidino-4-propyl-thiazole-5-carbonyl)-piperidin-3-ylmethoxy]-acetic acid.

19. The compound in accordance with claim 16, wherein the compound of formula la is (R)-[1-(2-guanidino-4-methyl-thiazole-5-carbonyl)-piperidin-3-yl-methoxy]-acetic acid.

20. The compound in accordance with claim 16, wherein the compound of formula Ia is rac [1-(4-tert-butyl-2-guanidino-thiazole-5-carbonyl)-piperidin-3-yl-methoxy]-acetic acid.

21. The compound in accordance with claim 13, wherein R³' is phenyl.

22. The compound in accordance with claim 21, wherein the compound of formula Ia is rac [1-(2-guanidino-4-phenyl-thiazole-5-carbonyl)-piperidin-3-yl-methoxy]-acetic acid.

23. The compound in accordance with claim 1, wherein the compound of formula I is ethyl (RS)-3-[[1-(2-guanidino-4-methyl-thiazole-5-carbonyl)-piperidine-3-carbonyl]-amino]-propionate.

24. The compound in accordance with claim 1, wherein the compound of formula I is (RS)-3-[[1-(2-guanidino-4-methyl-thiazole-5-carbonyl)-piperidine-3-carbonyl]-amino]-propionic acid hydrochloride.

25. The compound in accordance with claim 1, wherein the compound of formula I is [1-(2-guanidino-4-methyl-thiazole-5-carbonyl)-piperidin-4-yloxy]-acetic acid trifluoroacetate.

26. The compound in accordance with claim 1, wherein the compound of formula I is ethyl (RS)-3-[[1-(2-guanidino-thiazole-4-carbonyl)-piperidine-3-carbonyl]-amino]-propionate.

27. The compound in accordance with claim 1, wherein the compound of formula I is (RS)-3-[[1-(2-guanidino-thiazole-4-carbonyl)-piperidine-3-carbonyl]-amino]-propionic acid.

28. The compound in accordance with claim 1, wherein the compound of formula I is (R)-[1-(2-guanidino-4-methyl-thiazole-5-carbonyl)-pyrrolidin-3-ylmethoxy]-acetic acid.

29. The compound in accordance with claim 1, wherein the compound of formula I is (S)-[1-(2-guanidino-4-methyl-thiazole-5-carbonyl)-pyrrolidin-3-ylmethoxy]-acetic acid.

30. The compound in accordance with claim 1, wherein the compound of formula I is ethyl (RS)-[1-(2-guanidino-thiazole-5-carbonyl)-piperidin-3-ylmethoxy]-acetate.

31. The compound in accordance with claim 1, wherein the compound of formula I is (RS)-[1-(2-guanidino-thiazole-5-carbonyl)-piperidin-3-ylmethoxy]-acetic acid hydrochloride.

32. The compound in accordance with claim 1, wherein the compound of formula I is ethyl (RS)- and (SR)-3-[[(RS)-1-(2-guanidino-4-methyl-thiazole-5-carbonyl)-piperidine-3-carbonyl]-amino]-3-phenyl-propionate.

33. The compound in accordance with claim 1, wherein the compound of formula I is (SR)-3-[[(RS)-1-(2-guanidino-4-methyl-thiazole-5-carbonyl)-piperidine-3-carbonyl]-amino]-3-phenyl-propionic acid.

34. The compound in accordance with claim 1, wherein the compound of formula I is (RS)-3-[[(RS)-1-(2-guanidino-4-methyl-thiazole-5-carbonyl)-piperidine-3-carbonyl]-amino]-3-phenyl-propionic acid.

35. The compound in accordance with claim 1, wherein the compound of formula I is ethyl rac [1-(2-guanidino-thiazole-4-carbonyl)-piperidin-3-ylmethoxy]-acetate.

36. The compound in accordance with claim 1, wherein the compound of formula I is ethyl rac [1-(2-guanidino-4-methyl-thiazole-5-carbonyl)-piperidin-3-ylmethoxy]-acetate hexafluorophosphate.

37. The compound in accordance with claim 1, wherein the compound of formula I is ethyl rac [1-(2-guanidino-4-propyl-thiazole-5-carbonyl)-piperidin-3-ylmethoxy]-acetate.

38. The compound in accordance with claim 1, wherein the compound of formula I is ethyl rac [1-(2-guanidino-4-phenyl-thiazole-5-carbonyl)-piperidin-3-ylmethoxy]-acetate.

39. The compound in accordance with claim 1, wherein the compound of formula I is ethyl rac [1-(4-tert-butyl-2-guanidino-thiazole-5-carbonyl)-piperidin-3-ylmethoxy]-acetate.

40. The compound in accordance with claim 1, wherein the compound of formula I is ethyl rac [1-(4-cyclopentyl-2-guanidino-thiazole-5-carbonyl)-piperidin-3-ylmethoxy]-acetate.

41. The compound in accordance with claim 1, wherein the compound of formula I is rac [1-(2-guanidino-thiazole-4-carbonyl)-piperidin-3-ylmethoxy]-acetic acid.

42. The compound in accordance with claim 1, wherein the compound of formula I is rac [1-(2-guanidino-4-methyl-thiazole-5-carbonyl)-piperidin-3-yl-methoxy]-acetic acid.

43. The compound in accordance with claim 1, wherein the compound of formula I is rac [1-(2-guanidino-4-propyl-thiazole-5-carbonyl)-piperidin-3-ylmethoxy]-acetic acid.

44. The compound in accordance with claim 1, wherein the compound of formula I is rac [1-(2-guanidino-4-phenyl-thiazole-5-carbonyl)-piperidin-3-ylmethoxy]-acetic acid.

45. The compound in accordance with claim 1, wherein the compound of formula I is rac [1-(4-tert-butyl-2-guanidino-thiazole-5-carbonyl)-piperidin-3-ylmethoxy]-acetic acid.

46. The compound in accordance with claim 1, wherein the compound of formula I is rac [1-(4-cyclopentyl-2-guanidino-thiazole-5-carbonyl)-piperidin-3-ylmethoxy]-acetic acid.

47. The compound in accordance with claim 1, wherein the compound of formula I is ethyl (S)-[1-(2-guanidino-4-methyl-thiazole-5-carbonyl)-piperidin-3-ylmethoxy]-acetate.

48. The compound in accordance with claim 1, wherein the compound of formula I is ethyl (R)-[1-(2-guanidino-4-methyl-thiazole-5-carbonyl)-piperidin-3-ylmethoxy]-acetate.

49. The compound in accordance with claim 1, wherein the compound of formula I is ethyl rac [1-(2-guanidino-4-methyl-thiazole-5-carbonyl)-pyrrolidin-2-ylmethoxy]-acetate.

50. The compound in accordance with claim 1, wherein the compound of formula I is ethyl rac 3-[1-(2-guanidino-4-methyl-thiazole-5-carbonyl)-piperidin-3-ylmethoxy]-propionate.

51. The compound in accordance with claim 1, wherein the compound of formula I is ethyl rac [4-(2-guanidino-4-methyl-thiazole-5-carbonyl)-morpholin-2-ylmethoxy]-acetate.

52. The compound in accordance with claim 1, wherein the compound of formula I is ethyl [1-(2-guanidino-4-methyl-thiazole-5-carbonyl)-piperidin-4-yl-methoxy]-acetate.

53. The compound in accordance with claim 1, wherein the compound of formula I is (S)-[1-(2-guanidino-4-methyl-thiazole-5-carbonyl)-piperidin-3-ylmethoxy]-acetic acid.

54. The compound in accordance with claim 1, wherein the compound of formula I is (R)-[1-(2-guanidino-4-methyl-thiazole-5-carbonyl)-piperidin-3-yl-methoxy]-acetic acid.

55. The compound in accordance with claim 1, wherein the compound of formula I is rac [1-(2-guanidino-4-methyl-thiazole-5-carbonyl)-pyrrolidin-2-yl-methoxy]-acetic acid.

56. The compound in accordance with claim 1, wherein the compound of formula I is rac 3-[1-(2-guanidino-4-methyl-thiazole-5-carbonyl)-piperidin-3-ylmethoxy]-propionic acid.

57. The compound in accordance with claim 1, wherein the compound of formula I is rac [4-(2-guanidino-4-methyl-thiazole-5-carbonyl)-morpholin-2-yl-methoxy]-acetic acid.

58. The compound in accordance with claim 1, wherein the compound of formula I is [1-(2-guanidino-4-methyl-thiazole-5-carbonyl)-piperidin-4-ylmethoxy]-acetic acid.

59. The compound in accordance with claim 1, wherein the compound of formula I is ethyl rac [1-[2-(3-benzyl-ureido)4-methyl-thiazole-5-carbonyl]-piperidin-3-ylmethoxy]-acetate.

60. The compound in accordance with claim 1, wherein the compound of formula I is rac [1-[2-(3-benzyl-ureido)4-methyl-thiazole-5-carbonyl]-piperidin-3-ylmethoxy]-acetic acid.

61. The compound in accordance with claim 1, wherein the compound of formula I is ethyl [1-(2-guanidino-thiazole-4-carbonyl)-piperidin-4-ylmethoxy]-acetate.

62. The compound in accordance with claim 1, wherein the compound of formula I is ethyl rac [1-(2-guanidino-4-methyl-thiazole-5-carbonyl)-piperidin-3-yl-oxy]-acetate.

63. The compound in accordance with claim 1, wherein the compound of formula I is ethyl rac [1-[4-methyl-2-(3-methyl-ureido)-thiazole-5-carbonyl]-piperidin-3-ylmethoxy]-acetate.

64. The compound in accordance with claim 1, wherein the compound of formula I is [1-(2-guanidino-thiazole-4-carbonyl)-piperidin-4-ylmethoxy]-acetic acid.

65. The compound in accordance with claim 1, wherein the compound of formula I is rac [1-(2-guanidino-4-methyl-thiazole-5-carbonyl)-piperidin-3-yloxy]-acetic acid.

66. The compound in accordance with claim 1, wherein the compound of formula I is rac [1-[4-methyl-2-(3-methyl-ureido)-thiazole-5-carbonyl]-piperidin-3-ylmethoxy]-acetic acid.

67. A process for the manufacture of a compound having the formula:

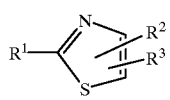
(I)

wherein
R$^1$ is

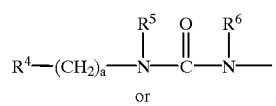
or
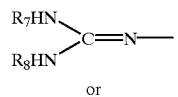
or
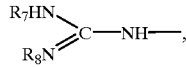

R$^2$ is

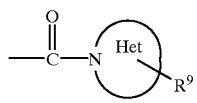

in which Het is a 5- to 8-atom heterocyclic ring that is substituted with R$^9$, the heterocyclic ring contains the depicted nitrogen atom and one atom selected from the group consisting of C, O, N, and S, with the remaining atoms in the heterocyclic ring being C;

R$^3$ is hydrogen, alkyl, cycloalkyl, aryl, aralkyl, or heteroaryl;

R$^4$ is hydrogen, alkyl, cycloalkyl, aryl or, heteroaryl;

R$^5$, R$^6$, R$^7$ and R$^8$ are each independently hydrogen, alkyl, or cycloalkyl, or R$^7$ and R8 together with the N atoms to which they are attached form a 5- to 8-membered heterocyclic ring or 5- to 8-membered heterocyclic ring that is substituted with alkyl;

R$^9$ is

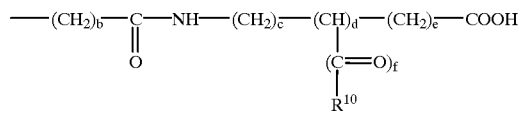

or —(CH$_2$)$_g$—(O)$_h$—(CH$_2$)$_i$—COOH,

R$^{10}$ is aryl, aralkyl, heterocyclyl, or an α-amino acid bonded via the amino group;

a, b, and c are each independently integers from 0 to 4, d is 0 or 1, e is an integer from 0 to 4, when d is 0 then f is 0, the sum of c, d and e is an integer from 1 to 4, f is 0 or 1, g is an integer from 0 to 5, h is 0 or 1, when h is 1 i is not 0, the sum of g, h and i is an integer from 2 to 5;

or a pharmaceutically usable salts and esters thereof;

which comprises reacting a thiazolecarboxylic acid of formula:

(II)

with an amine of formula:

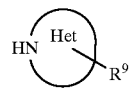
(III)

or a salt or ester thereof, wherein R$^1$, R$^3$, R$^9$ and Het are as above.

68. A pharmaceutical composition, which comprises:

(a) a compound of the formula:

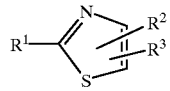
(I)

wherein
R$^1$ is

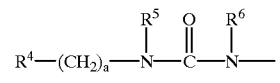
or

-continued

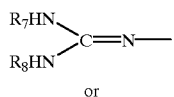

or

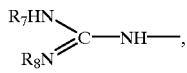

$R^2$ is

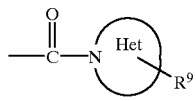

in which Het is a 5- to 8-atom heterocyclic ring that is substituted with $R^9$, the heterocyclic ring contains the depicted nitrogen atom and one atom selected from the group consisting of C, O, N, and S, with the remaining atoms in the heterocyclic ring being C;

$R^3$ is hydrogen, alkyl, cycloalkyl, aryl, aralkyl, or heteroaryl;

$R^4$ is hydrogen, alkyl, cycloalkyl, aryl or, heteroaryl;

$R^5$, $R^6$, $R^7$ and $R^8$ are each independently hydrogen, alkyl, or cycloalkyl, or $R^7$ and $R^8$ together with the N atoms to which they are attached form a 5- to 8-membered heterocyclic ring or 5- to 8-membered heterocyclic ring that is substituted with alkyl;

$R^9$ is

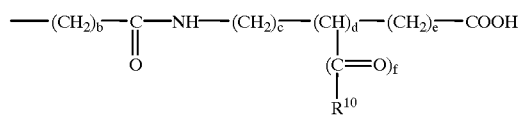

or $-(CH_2)_g-(O)_h-(CH_2)_i-COOH$, $R^{10}$ is aryl, aralkyl, heterocyclyl, or an (α-amino acid bonded via the amino group;

a, b, and c are each independently integers from 0 to 4, d is 0 or 1, e is an integer from 0 to 4, when d is 0 then f is 0, the sum of c, d and e is an integer from 1 to 4, f is 0 or 1, g is an integer from 0 to 5, h is 0 or 1, when h is 1 i is not 0, the sum of g, h and i is an integer from 2 to 5;

or a pharmaceutically usable salts and esters thereof; and (b) a pharmaceutically acceptable carrier.

* * * * *

UNITED STATES PATENT AND TRADEMARK OFFICE
CERTIFICATE OF CORRECTION

PATENT NO. : 6,001,855
DATED : December 14, 1999
INVENTOR(S) : Alig et al.

It is certified that error appears in the above-identified patent and that said Letters Patent is hereby corrected as shown below:

Column 29, claim 1, line 47, "$-(CH_2)_g-(O)_h-(CH_2)-COOH$," should be -- $-(CH_2)_g-(O)_h-(CH_2)_i-COOH$, --

Column 33, claim 59, line 6, "ureido)4-methyl-" should be -- ureido)-4-methyl- --

Column 33, claim 60, line 8, "-ureido)4-" should be -- -ureido)-4- --

Signed and Sealed this

Eighth Day of August, 2000

Attest:

Q. TODD DICKINSON

Attesting Officer

Director of Patents and Trademarks